United States Patent
Korri-Youssoufi et al.

(10) Patent No.: US 10,895,551 B2
(45) Date of Patent: Jan. 19, 2021

(54) SYSTEM FOR ELECTROCHEMICAL DETECTION OF MOLECULES OF INTEREST

(71) Applicants: UNIVERSITE PARIS-SUD, Orsay (FR); CENTRE NATIONAL DE LA RECHERCHE SCIENTIFIQUE, Paris (FR)

(72) Inventors: Hafsa Korri-Youssoufi, Bruyères-le-Châtel (FR); Anna Miodek, Orsay (FR); Nawel Mejri, Bretigny-sur-Orge (FR)

(73) Assignees: UNIVERSITE PARIS-SUD, Orsay (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 39 days.

(21) Appl. No.: 15/773,517

(22) PCT Filed: Nov. 14, 2016

(86) PCT No.: PCT/EP2016/077564
§ 371 (c)(1),
(2) Date: May 3, 2018

(87) PCT Pub. No.: WO2017/081315
PCT Pub. Date: May 18, 2017

(65) Prior Publication Data
US 2019/0250120 A1 Aug. 15, 2019

(30) Foreign Application Priority Data
Nov. 13, 2015 (FR) ..................... 15 60917

(51) Int. Cl.
*G01N 27/327* (2006.01)
*C12Q 1/6825* (2018.01)
*G01N 33/543* (2006.01)

(52) U.S. Cl.
CPC ....... *G01N 27/3276* (2013.01); *C12Q 1/6825* (2013.01); *G01N 27/3277* (2013.01); *G01N 27/3278* (2013.01); *G01N 33/5438* (2013.01)

(58) Field of Classification Search
CPC .......... G01N 27/3276; G01N 27/3277; G01N 27/3278; G01N 33/5438; C12Q 1/6825
See application file for complete search history.

(56) References Cited

U.S. PATENT DOCUMENTS

2014/0174950 A1   6/2014 Gooding et al.

OTHER PUBLICATIONS

J. H. Wong, et al. ("Proteins with antifungal properties and other medicinal applications from plants and mushrooms", Applied Microbiology and Biotechnology, 87(4):p. 1221-1235, Jul. 2010.*
G. Liu, et al. "The modification of glassy carbon and gold electrodes with aryl diazonium salt: The impact of the electrode materials on the rate of heterogeneous electron transfer", Chemical Physics, 319(1-3): p. 136-146, Dec. 2005.*

(Continued)

*Primary Examiner* — J. Christopher Ball
(74) *Attorney, Agent, or Firm* — Greer, Burns & Crain, Ltd.

(57) ABSTRACT

A system for "signal-on" electrochemical detection of molecules of interest and to a method implementing said system.

18 Claims, 9 Drawing Sheets
Specification includes a Sequence Listing.

(56) References Cited

OTHER PUBLICATIONS

G. Li, et al. "Dendrimers-based DNA biosensors for highly sensitive electrochemical detection of DNA hybridization using reporter probe DNA modified with Au nanoparticles", Biosensors and Bioelectronics, 24(11): p. 3281-3287, Jul. 2009.*

Farjami et al., "'Off-On' Electrochemical Hairpin-DNA-Based Genosensor for Cancer Diagnostics," Analytical Chemistry (2011), 83(5), pp. 1594-1602.

Li et al., "Carbon Nanotube-Polyamidoamine Dendrimer Hybrid-Modified Electrodes for Highly Sensitive Electrochemical Detection of MicroRNA24", Analytical Chemistry (2015), 87(9), pp. 4806-4813.

Miodek et al., "Direct Electrochemical Detection of PB1-F2 Protein of Influenza A Virus in Infected Cells", Biosensors and Bioelectronics (2014), vol. 59, pp. 6-13.

Miodek et al., "E-DNA Sensor of *Mycobacterium tuberculosis* Based on Electrochemical Assembly of Nanomaterials (MWCNTs/PPy/PAMAM)", Analytical Chemistry (2015), 87(18), pp. 9257-9264.

Miodek et al., "Electrochemical Aptasensor of Cellular Prion Protein Based on Modified Polypyrrole with Redox Dendrimers", Biosensors and Bioelectronics (2014), vol. 56, pp. 104-111.

Miodek et al., "Electrochemical Aptasensor of Human Cellular Prion Based on Multiwalled Carbon Nanotubes Modified with Dendrimers: A Platform for Connecting Redox Markers and Aptamers", Analytical Chemistry (2013), 85(16), pp. 7704-7712.

Miodek et al., "Electrochemical Functionalization of Polypyrrole Through Amine Oxidation of Poly(Amidoamine) Dendrimers: Application to DNA Biosensor", Talanta (2016), vol. 154, pp. 446-454.

Xiao et al., "Label-Free Electrochemical Detection of DNA in Blood Serum via Target-Induced Resolution of an Electrode-Bound DNA Pseudoknot", Journal of the American Chemical Society (2007), 129(39), pp. 11896-11897.

Zribi et al., "A Microfluidic Electrochemical Biosensor Based on Multiwall Carbon Nanotube/Ferrocene for Genomic DNA Detection of *Mycobacterium tuberculosis* in Clinical Isolates", Biomicrofluidics (2016), 10(6), pp. 014115-1-014115-12.

French Search Report from French Patent Application No. 1560917, dated Apr. 14, 2016.

International Search Report from International Patent Application No. PCT/EP2016/077564, dated Feb. 6, 2017.

* cited by examiner

Target DNA

● Nanoparticles, Redox marker Fc, DNA

Toxin

● Nanoparticles, Redox marker Fc, DNA of aptamer type

SEQUENCE LISTING

```
<160> NUMBER OF SEQ ID NOS: 6

<210> SEQ ID NO 1
<211> LENGTH: 15
<212> TYPE: DNA
<213> ORGANISM: Artificial Sequence
<220> FEATURE:
<223> OTHER INFORMATION: ssDNA probe

<400> SEQUENCE: 1
gatacttcta tcacc                                                      15

<210> SEQ ID NO 2
<211> LENGTH: 15
<212> TYPE: DNA
<213> ORGANISM: Artificial Sequence
<220> FEATURE:
<223> OTHER INFORMATION: Synthetic DNA of interest

<400> SEQUENCE: 2
ggtgatagaa gtatc                                                      15

<210> SEQ ID NO 3
<211> LENGTH: 14
<212> TYPE: DNA
<213> ORGANISM: Artificial Sequence
<220> FEATURE:
<223> OTHER INFORMATION: Non-complementary oligonucleotide

<400> SEQUENCE: 3
cattccctct tagg                                                       14

<210> SEQ ID NO 4
<211> LENGTH: 18
<212> TYPE: DNA
<213> ORGANISM: Artificial Sequence
<220> FEATURE:
<223> OTHER INFORMATION: PCR probe

<400> SEQUENCE: 4
ccgactgttg gcgctggg                                                   18

<210> SEQ ID NO 5
<211> LENGTH: 25
<212> TYPE: DNA
<213> ORGANISM: Artificial Sequence
<220> FEATURE:
<223> OTHER INFORMATION: Oligonucleotide probe targeting the Hepatitis C
      virus

<400> SEQUENCE: 5
tcaacttcgg gaatctcaat gttag                                           25

<210> SEQ ID NO 6
<211> LENGTH: 36
<212> TYPE: DNA
<213> ORGANISM: Artificial Sequence
<220> FEATURE:
<223> OTHER INFORMATION: Aptamer probe targeting OTA
```

```
<400> SEQUENCE: 6
gatcgggtgt gggtggcgta aagggagcat cggaca                                36
```

SYSTEM FOR ELECTROCHEMICAL DETECTION OF MOLECULES OF INTEREST

REFERENCE TO AN ELECTRONIC SEQUENCE LISTING

The contents of the electronic sequence listing (12R8059.txt; Size: 1.42 KB; and Date of Creation: Aug. 20, 2018) is herein incorporated by reference in its entirety and contains no new subject matter.

BACKGROUND

The present invention relates to a system for electrochemical detection of molecules of interest as well as a method for implementing said system.

Measuring a biological molecule, in particular a DNA molecule or a pathogenic protein molecule, in a sample is very useful and necessary in different fields of analysis such as diagnostics, the environment or the agri-food industry. This detection is currently carried out by analysis systems that require a technical environment and bulky tools, such as PCR.

In order to be used in the field of clinical analysis, the detection system should be sensitive and make it possible to quantify in a sample to be analyzed the presence of pathogens even at very low concentrations, for example of the order of the femtomolar ($10^{-15}$ mol/l), with a very low probability of false positives.

Electrochemical devices meet this challenge. It is known from the prior art that biosensors indicate the presence of a molecule of interest, in particular a DNA molecule, using a DNA probe that is complementary to the DNA molecule of interest and a redox probe producing an electrochemical signal.

Two types of biosensor can be identified among the electrochemical detection devices of the prior art: "signal-off" biosensors and "signal-on" biosensors.

"Signal-off biosensors" produce a decrease in the electrochemical signal after hybridization of the DNA probe with the DNA molecule of interest. In fact, formation of double-stranded DNA forces the redox probe to move away from the surface of the electrode, thus reducing the transfer of electrons between the redox probe and the electrode.

For example, Farjami et al. (*Anal. Chem.*, 2011, 83 (5), pp 1594-1602) describe detecting DNA using an electrochemical method involving a biosensor, which comprises:

a hairpin DNA probe immobilized at its 3' end on a gold electrode, and a redox probe connected at the 5' end of said DNA probe located close to said electrode via the hairpin structure of the DNA probe.

The drawback with this type of biosensor is the uncertainty regarding the origin of the signal decrease which can be due to the degradation or ageing of the redox probe.

"Signal-on" biosensors induce an increase in the electrochemical signal from the moment the DNA probe is hybridized with the DNA molecule of interest. These biosensors require:

a preliminary structuring specific to the DNA probe to make it possible to move the redox probe away from the electrode surface or to mask it, and structural adaptation of the DNA probe for each DNA molecule of interest.

When the biosensor comes into contact with a target DNA molecule, the interaction between the DNA probe and the biosensor frees the redox probe which can then move closer to the electrode and create an electrochemical signal.

The DNA probe implemented in this type of biosensor can be in the form of a double-stranded, or even a triple-stranded structure, and optionally configured in the form of a hairpin.

Xiao et al. (*J. Am. Chem. Soc.*, 2007, 129, 11896-11897) describe an electrochemical DNA biosensor containing a single-stranded DNA probe labelled with a redox probe. Said DNA probe forms a triple-stranded structure making it possible to move the redox probe away from the electrode surface. During hybridization with the DNA probe, the redox probe comes into contact with the conductive surface resulting in an increase in current. The electrochemical biosensor has a sensitivity threshold limited to 5 nM.

The main drawback of known biosensors of the "signal-on" type is the necessary and complex structuring of the DNA probe which requires an optimization for each of DNA molecule of interest to be detected. In addition, these DNA electrochemical biosensors have an unsatisfactory detection sensitivity threshold.

Thus, the need still exists, in particular in the fields of clinical and food analysis, to develop an electrochemical biosensor making it possible to detect molecules of interest at very low concentrations without preliminary structuring or optimization of the DNA probe.

SUMMARY

A subject of the present invention is to make available an electrochemical detection system of the "signal-on" biosensor type, the sensitivity of which is very high and the adaptation of the DNA probe of which is not necessary.

The system for electrochemical detection of molecules of interest according to the present invention comprises:

a conductive material, at least one nanomaterial bearing positive functions, covalently bound to said conductive material, at least one redox molecule, and at least one single-stranded oligonucleotide probe targeting a molecule of interest, said redox molecule being covalently bound to said nanomaterial;

said oligonucleotide probe being covalently bound to said nanomaterial or to the redox molecule;

the number of positive functions of said nanomaterial being greater than the number of oligonucleotide probes.

The present invention is based on the surprising fact that the interaction between the negative charges of the phosphate groups of the oligonucleotide probe and the positive charges of the nanomaterial allows a three-dimensional organization such that it blocks the transfer of electrons from the redox molecule to the conductive material.

In the absence of the molecule of interest to be detected, the negatively charged phosphate groups interact with the positive functions present at the surface of the nanomaterial. These interactions of the ionic type involve folding the oligonucleotide probe on the nanomaterial with the result of preventing the transfer of electrons from the redox molecule to the surface of the nanomaterial.

From the moment that the molecule of interest to be detected is present in the sample analyzed, the reaction between the molecule of interest and the oligonucleotide probe changes the conformation of the oligonucleotide probe, for example a double-stranded DNA forming between a DNA molecule of interest to be detected and the oligonucleotide probe, and interrupts the interaction between the latter and the nanomaterial, which makes it possible to unmask the redox molecule and allow the transfer of electrons from the redox molecule to the surface of the nanomaterial.

This transfer or electrons generates a faradic current which can be detected by an electroanalysis method.

Within the framework of the invention, the amperage of this current is proportional to the number of molecules of interest interacting with the oligonucleotide probe.

As a result, measuring the electric current makes it possible to show the concentration of the molecule of interest in the sample analyzed.

One of the advantages of the system of the present invention is its increased sensitivity to a molecule of interest. The system of the present invention is capable of quantifying the molecules of interest at very low concentrations, in particular of the order of the femtomolar ($10^{-15}$ mol/L).

Another advantage of the system of the present invention is that the single-stranded oligonucleotide probe does not require either a specific preliminary structuring or optimization with regard to different molecules of interest, due to the interactions between the negative charges of the phosphate groups of the oligonucleotide probe and the positive charges of the nanomaterial allowing a three-dimensional configuration such that the transfer of electrons is prevented.

In addition, unlike the known electrochemical detection systems, the detection system according to the invention limits considerably the appearance of false positives, due to the high specificity of the oligonucleotide probe and the strong blocking of the transfer of electrons.

According to the invention, by "oligonucleotide probe" is meant a single-stranded oligonucleotide of 10 to 50 nucleotides, in particular of 10 to 25 nucleotides, specific to a molecule of interest, functionalization of the 5' or 3' end of which allows covalent bonding between said probe and the redox molecule.

By way of example, said oligonucleotide can be functionalized by an amine or an acid. The amine or acid can be separated from the end of the oligonucleotide by a hydrocarbon linker containing 1 to 10 carbon atoms.

Said single-stranded oligonucleotide can be an RNA molecule or a DNA molecule, optionally forming an aptamer.

As a "molecule of interest" capable of being detected by the electrochemical detection system of the invention a DNA molecule, an RNA molecule, a protein, a toxin or a chemical molecule can be mentioned.

A DNA molecule of interest can be an isolated natural genomic DNA molecule, a viral DNA molecule, a synthesized cDNA molecule, or a product of PCR.

An RNA molecule of interest can be an gRNA molecule, an mRNA molecule, a pre-mRNA molecule, an siRNA molecule, a microRNA molecule, an RNAi molecule, a tRNA molecule, an rRNA molecule, an snRNA molecule or satellite RNA molecule.

When the molecule of interest is a DNA molecule or an RNA molecule, the oligonucleotide probe targeting said molecule is a DNA molecule or an RNA molecule having a complementary sequence. The presence of said molecule of interest in a sample leads to the formation of a double-stranded structure which is placed perpendicular to the surface of the nanomaterial.

When the molecule of interest is a protein or a toxin, the oligonucleotide probe targeting said molecule forms an aptamer on which said molecule of interest can become fixed as a ligand. The sequence of such an oligonucleotide probe can be determined according to the knowledge of a person skilled in the art or selected according to a traditional method, such as the SELEX (systematic evolution of ligands by exponential enrichment) technique.

According to the present invention, by "redox molecule" is meant a molecule that is active for an oxidation-reduction reaction and capable of producing an electrochemical signal that is measurable using an electroanalysis method associated with the transfer of electrons between said redox molecule and the conductive material. This electrochemical signal makes it possible to indicate the presence of a molecule of interest complementary to the oligonucleotide probe.

According to an embodiment of the invention, said redox molecule is covalently bound to both said nanomaterial and the oligonucleotide probe, the number of positive functions of said nanomaterial being quite high in order to block the transfer of electrons from the redox molecules to the conductive material, and in particular the number of positive functions of said nanomaterial being greater than the number of oligonucleotide probes.

This type of detection system according to the invention allows simultaneous detection of several molecules of interest.

A particular embodiment of the invention relates to an electrochemical detection system comprising:
  at least two types of redox molecules the oxidation-reduction potentials of which are different, and
  at least two types of single-stranded oligonucleotide probes each targeting a different molecule of interest,
the same type of oligonucleotide probes being bound to the same type of redox molecules.

The use of at least two types of redox molecules, each bound to a type of oligonucleotide probe in said electrochemical detection system allows simultaneous detection of at least two different molecules of interest in a sample. The presence of each molecule of interest is indicated respectively by a different electrochemical signal.

Said system is particularly useful for detecting SNP (single-nucleotide polymorphism) in a sample.

In an advantageous embodiment, the invention relates to an electrochemical detection system comprising:
  two types of redox molecules the oxidation-reduction potentials of which are different, and
  two types of single-stranded oligonucleotide probes, each targeting a different molecule of interest,
the same type of oligonucleotide probes being bound to the same type of redox molecules.

In another advantageous embodiment, the invention relates to an electrochemical detection system comprising:
  three types of redox molecules the oxidation-reduction potentials of which are different, and
  three types of single-stranded oligonucleotide probes, each targeting a different molecule of interest,
the same type of oligonucleotide probes being bound to the same type of redox molecules.

According to another embodiment of the invention, the system for electrochemical detection of molecule(s) of interest according to the present invention comprises said redox molecule and said oligonucleotide probe covalently bound to said nanomaterial, the number of positive functions of said nanomaterial being quite high in order to block the transfer of electrons from the redox molecule to the conductive material, and in particular the number of positive functions of said nanomaterial being greater than the number of oligonucleotide probes.

This type of detection system has the advantage of being less tedious and quicker to synthesize since the redox molecule has a single functional group.

The redox molecule used in the electrochemical detection system of the invention can be any redox molecule known to a person skilled in the art, and more particularly selected from the group comprising ferrocene, quinone, methylene blue, metalloporphyrins and viologen.

In an embodiment, said redox molecule can be functionalized beforehand according to a conventional method in order to covalently bind to a nanomaterial.

For example, a redox molecule can be functionalized by an acid in order to introduce a —COOH group. A redox molecule thus modified can react, optionally with the help of a coupling agent, with the amines located on the surface of a nanomaterial. More particularly the redox molecule can be functionalized so as to be able to react both with the oligonucleotide probe and to the nanomaterial covalently.

In an embodiment where the oligonucleotide probe is covalently bound to the nanomaterial, said probe is functionalized so as to be able to react with said nanomaterial without reacting with said redox molecule which is also covalently bound to said nanomaterial.

By way of example, an oligonucleotide probe can be modified by a —COOH group so as to covalently bind with the amine functions of the nanomaterial.

Advantageously, the functionalization carried out beforehand is done by "click chemistry".

Within the framework of the present invention, the terms "redox molecules" and "redox probe" can replace each other.

By "number of positive functions of said nanomaterial being quite high" is meant that the number of positive functions is sufficiently great as to allow effective folding of the oligonucleotide probes on said positive functions.

By "the number of positive functions of said nanomaterial being greater than the number of oligonucleotide probes" is meant that the number of positive functions borne by said nanomaterial is greater than the number of oligonucleotide probes covalently bound to the nanomaterial via a redox molecule, which ensures efficient blocking of the transfer of electrons between the negative charges of the phosphate groups of the oligonucleotide probe and the positive charges of the nanomaterial bearing positive functions.

The number of positive functions borne by a nanomaterial and the number of oligonucleotide probes can respectively be determined according to methods known in the prior art.

According to the present invention, the nanomaterial bearing positive functions of said electrochemical detection system is selected from the group comprising:
 a dendrimer, preferentially a dendrimer of the poly(amidoamine) type, in particular of second, fourth or sixth generation (respectively G2, G4 or G6),
 metal particles such as gold nanoparticles,
 magnetic nanoparticles, such as iron oxide,
 hybrid nanomaterials based on chitosan, and
 conductive polymers, optionally modified by positive functions, such as polypyrrole, polyaniline or polyparaphenylene.

In an advantageous embodiment, the nanomaterial used according to the electrochemical detection system according to the invention is a dendrimer of the poly(amidoamine) (PAMAM) type, the structure of which is globular and the diameter of which, as well as the number of primary amine groups present at the surface of said dendrimer increases as a function of the number of generations, also:
 the G2 PAMAMs have a diameter of approximately 2.9 nm and have 16 primary amine groups,
 the G4 PAMAMs have a diameter of approximately 4.5 nm and have 64 primary amine groups, and
 the G6 PAMAMs have a diameter of approximately 6.7 nm and have 256 primary amine groups.

Using PAMAMs bearing a high density of amine groups makes it possible not only to facilitate functionalization by different substances, such as different redox molecules, but also to increase the sensitivity threshold of said detection system.

In a more advantageous embodiment, the nanomaterial used in an electrochemical detection system of the invention is the G4 PAMAMs.

In another advantageous embodiment, the nanomaterial used in an electrochemical detection system of the invention is functionalized gold nanoparticles. The gold nanoparticles have a good surface to volume ratio making it possible to obtain materials structured in three dimensions that are useful in the construction of electrochemical sensors.

By way of example, gold nanoparticles can be functionalized by cystamine in order to become a nanomaterial bearing positive functions. Cystamine comprises two sulphur atoms able to attach to the surface of the gold nanoparticles and leave free amine groups. The latter can be functionalized subsequently.

In another advantageous embodiment, the nanomaterial used in a detection system of the invention is optionally functionalized gold nanoparticles associated with G4 PAMAMs. The gold nanoparticles improve conductivity and further increase the electrochemical signal. The association of gold nanoparticles with the PAMAMs makes is possible to expand the dynamic range of the detection system of the invention.

The nanomaterial is bound to the conductive material by covalent bonding. A person skilled in the art will know how to select a method appropriate for the nature of the nanomaterial for depositing it on the conductive material.

For example, the PAMAMs can be deposited on the surface of a carbon electrode by electrodeposition. Oxidation of the amine groups of the PAMAMs creates a cationic radical —NH.$^+$ which interacts with the C=C group on the carbon surface, thus implementing a covalent grafting.

The gold particles functionalized by cystamine can be deposited, via amine groups, on the surface of a carbon electrode by using N-(3-dimethylaminopropyl)-N'-ethylcarbodiimide hydrochloride/N-hydroxysuccinimide (EDC/NHS) beforehand in order to functionalize said electrode.

In the electrochemical detection system of the invention, said conductive material acts as an electrode and provides a regular surface for attaching nanomaterials. Said material can be formed from carbon, in particular from carbon nanotubes, glassy carbon, graphite, graphene or a metal.

In a particular embodiment, said conductive material is a micro- or a nanoelectrode which can be dispersed in a solution.

According to another particular embodiment of the invention, the conductive material is absent from said detection system when said nanomaterial bearing positive functions is conductive.

For example, gold nanoparticles, metal nanoparticles (platinum, silver, etc.), metal oxides, quantum dots, graphite or graphene can be both the nanomaterial bearing positive functions and the conductive material.

An electrochemical detection system according to the invention can be used in:
 detecting pathogens, such as bacteria, viruses, parasites or biomarkers, such as oncological biomarkers, Alzheimer's disease biomarkers, Parkinson's disease biomarkers, etc., in a biological sample, which allows in vitro or in vivo diagnosis of diseases, identifying resistance of at least one pathogen to a medicinal product, detecting a pathogen or a toxin in an agri-food, or pharmaceutical sample or an effluent, for example bacterial toxins of the genus *Salmonella, Staphylococcus, Aeromonas, Escherichia coli, Listeria, Clostridium*, etc., and monitoring the presence or the absence of at least one medicinal product in biological fluids, in particular within the framework of chronic and/or intensive treatments such as chemotherapy or taking anticoagulants.

To this end, the electrochemical detection system according to the invention is used according to the following steps:

i. bringing into contact said electrochemical detection system and the sample, and ii. detecting at least one pathogen, at least one toxin or at least one medicinal product of interest.

By way of example, said electrochemical detection system according to the invention can be used for detecting Ochratoxin A.

Said electrochemical detection system can also be used for detecting or distinguishing SNP sites.

According to a particular embodiment, said electrochemical detection system of the invention contains an oligonucleotide probe of sequence SEQ ID NO: 4. Said system can be used for detecting *Mycobacterium tuberculosis* that is resistant to rifampicin by distinguishing the SNP (TCG/TTG) site within the *Mycobacterium tuberculosis* genome.

A subject of the invention is also to propose a method for electrochemical detection of molecules of interest within a sample.

Said method comprises the following steps:

(i) bringing a detection system according to the invention into contact with a sample capable of containing a molecule of interest, and (ii) electrochemical measurement of the redox signal specific to said molecule of interest.

By "electrochemical measurement" is meant the measurement of a variation in the oxidation-reduction potential of the redox molecule or the measurement of a variation in the amperometric type by variation in the oxidation current observed at a given potential or the measurement of a change in impedance at a given potential. These variations are measured according to methods that are well known to a person skilled in the art.

When a molecule of interest is present in a sample, its interaction with the oligonucleotide probe makes it possible to interrupt the interaction between said oligonucleotide probe and the nanomaterial bearing positive functions, in order to unmask the redox molecule, thus creating a faradic current.

Electrochemical measurement makes it possible to detect this current, represented by a redox signal. As a result, this signal is specific to said molecule of interest.

The electrochemical measurement for implementing the invention can be a potentiometric measurement, an impedance measurement, a coulometric measurement or an amperometric measurement.

In an advantageous embodiment, the electrochemical measurement is implemented by an amperometric measurement.

Measurement of the electric current can be carried out by means of known amperometric techniques, preferentially by potential scanning voltammetry that can be linear, cyclic, pulsed or even of the potential change type, such as chronoamperometry.

According to the invention, the sample should have a pH for which, within said detection system, the oligonucleotide probe is negatively charged and the nanomaterial is the bearer of positive charges.

In particular, the sample should have a pH comprised between 6 and 7.

According to the invention, said sample can be a biological sample.

Advantageously, this sample can have been taken from a patient for diagnostic reasons. The sample can be, for example, urine, blood, serum, plasma, cellular extracts or a body fluid.

According to the invention, the electrochemical detection method can comprise, in addition to steps (i) and (ii) and after step (ii), quantitative analysis of said molecule of interest. Quantization of the molecule(s) of interest is carried out using a calibration curve established beforehand according to one of the methods known to a person skilled in the art.

According to a particular embodiment, the invention relates to a method for multiple electrochemical detection of at least two types of molecules of interest.

Said method comprises the following steps:

(i) bringing a detection system comprising at least two types of redox molecules and at least two types of oligonucleotide probes, as described above, into contact with a sample capable of containing said molecules of interest;

(ii) measuring the redox signals specific to said molecules of interest.

Said method allows simultaneous detection of at least two types of molecules of interest.

The present invention also relates to a modified support for preparing s the detection system.

Said support comprises:
a conductive material,
a nanomaterial bearing positive functions, and
at least one redox molecule,
said nanomaterial being situated between said conductive material and said redox molecule and being covalently bound to the latter two.

Said support makes it possible to provide a platform ready to be functionalized by oligonucleotide probes according to the requirements of the user.

Said support can bound, via a functionalized redox molecule, to an oligonucleotide the 5' end of which is also modified.

Said support can be prepared according to the following method:

covering a conductive material with a nanomaterial bearing positive functions, forming covalent bonds between said conductive material and said nanomaterial;

functionalizing said nanomaterial bearing positive functions using at least one redox molecule that is also functionalized.

The invention also provides the method for preparing said electrochemical detection system which comprises:

(i) bringing said modified support as described above into contact with at least one functionalized oligonucleotide targeting a molecule of interest;

(ii) forming covalent bonds between the aforementioned modified support and said functionalized oligonucleotide.

During step (ii), the formation of a covalent bond between said modified support and said functionalized oligonucleotide can either be carried out between said functionalized oligonucleotide and said nanomaterial or between said functionalized oligonucleotide and said redox molecule.

The method for preparing said electrochemical detection system according to the invention requires prior functionalization of the oligonucleotide probe at the 3' or 5' end and prior functionalization of the redox molecule. When they are brought into contact, said functionalized oligonucleotide and the redox molecule form covalent bonds via these functional groups.

By "functionalized oligonucleotide" is meant an oligonucleotide the 5' or 3' end of which is modified by an active function, such as an amine, an acid, an azide, an alkyne, a thiol, etc., and capable of implementing a rapid chemical reaction of the "click chemistry" type with a compound containing another compatible active function.

Advantageously, the present invention also proposes an ultrasensitive detection kit for molecules of interest that can be used in early or ambulant diagnosis.

Said kit comprises:
(i) a modified support as described above, and
(ii) at least one oligonucleotide targeting a molecule of interest.

Said kit allows users to prepare an electrochemical detection system according to the invention themselves at their convenience and makes it possible to avoid ageing or degradation of the oligonucleotide probe which can give false negatives. In order to bind to the redox molecules contained in said modified support, said oligonucleotide is modified at its 5' end by adding an amine group.

According to an embodiment of the invention, the kit for preparing said electrochemical detection system according to the invention can comprise:
at least two types of redox molecules the oxidation-reduction potentials of which are different, and
at least two types of single-stranded oligonucleotide probes,
each type of oligonucleotide probe being bound to a redox molecule the oxidation-reduction potentials of which are different from each another.

BRIEF DESCRIPTION OF THE DRAWINGS

FIGS. 1 to 10 and the examples below illustrate the present invention.

FIG. 1 shows the detection system according to the invention in the absence and in the presence of a molecule of interest, in particular a DNA molecule.

FIG. 2 shows the detection system according to the invention in the absence and in the presence of a molecule of interest, in particular an aptamer.

FIG. 6 shows the specificity of the detection system according to the invention when the oligonucleotide probe is a synthetic DNA molecule, and in particular in the detection of the hepatitis C virus.

FIG. 7b shows the selectivity of said detection system for Ochratoxin A vs Ochratoxin B.

FIG. 8 shows the specificity of the system for detecting Ochratoxin A according to the invention in which the nanomaterial used is G2 PAMAM modified with naphthoquinone as the redox probe and the aptamer specific to Ochratoxin A.

FIG. 9 shows the specificity of the detection system according to the invention containing magnetic iron oxide ($Fe_3O_4$) nanoparticles coated with chitosan and modified with the naphthoquinone redox probe for detecting Ochratoxin A.

FIG. 10 shows the specificity of the detection system according to the invention containing microspheres of chitosan and modified with the naphthoquinone redox probe for detecting Ochratoxin A.

DETAILED DESCRIPTION

EXAMPLES

Figure 1:
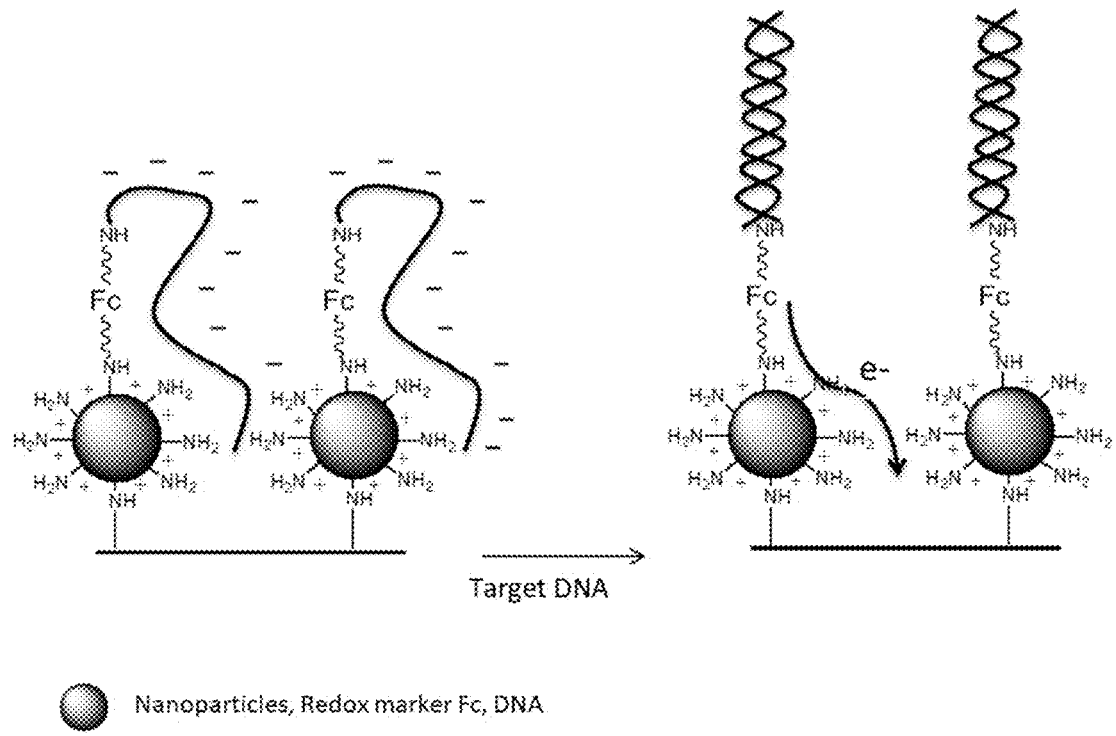
Figure 2:
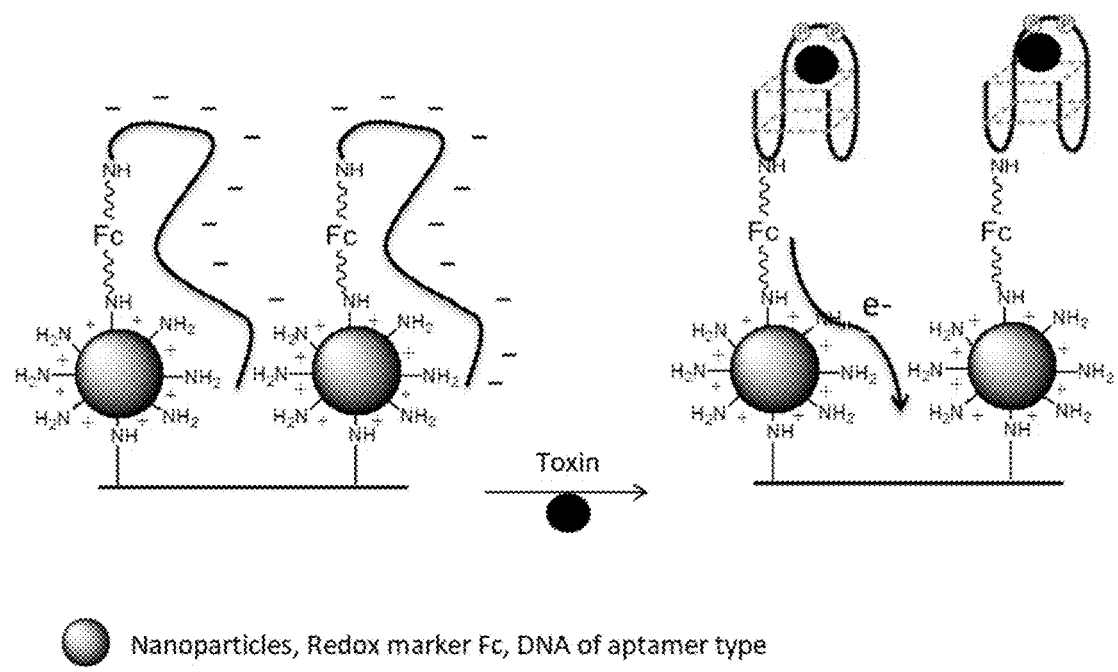

Materials and Methods
Products

Ferrocene $Fc(NHP)_2$ is synthesized according to methods known to a person skilled in the art.

The solution of phosphate buffer saline (PBS) pH=7.4 contains 10 mM of $Na_2HPO_4$, 1.8 mM of $KH_2PO_4$, 2.7 mM of KCl and 137 mM of NaCl. The PBS is prepared with double-distilled water and filtered through 0.22 μm membranes, then stored at 4° C. until use thereof.

The G4 PAMAM dendrimers are purified by 0.22 μM filtration membranes before use.

The gold nanoparticles (AuNPs) originate from Sigma-Aldrich in a 0.1 mM PBS solution and have a diameter of 5 nm.

The oligonucleotide probe used for studying the dynamic range of the system of the invention, hereinafter denoted "ssDNA probe", comprises an oligonucleotide of sequence SEQ ID NO: 1 (5'GAT-ACT-TCT-ATC-ACC3'), which is modified at the 5' end by the $NH_2C_6$— group.

Said probe targets a synthetic oligonucleotide of interest of sequence SEQ ID NO 2 (5'GGT-GAT-AGA-AGT-ATC3'), hereinafter denoted synthetic DNA molecule of interest. An oligonucleotide of sequence SEQ ID NO: 3 (5'CAT-TCC-CTC-TTA-GG3'), non-complementary with the aforementioned oligonucleotide probe, is used as a control.

Within the context of the experiment for the detection of resistant *Mycobacterium tuberculosis*, a PCR product with 411 bases is obtained from the rpoB gene of *Mycobacterium tuberculosis*.

cPCR is the PCR product obtained from 5 strains of *Mycobacterium tuberculosis* containing the mutation TCG/TTG in the rpoB gene which is responsible for the resistance to rifampicin. These 5 strains are 2-09, 7-09, 8-09, 10-09 and 11-09.

ncPCR is the PCR product obtained from the non-mutated rpoB gene from wild strains of *Mycobacterium tuberculosis*.

The oligonucleotide probe targeting cPCR, hereinafter denoted "PCR probe", comprises an oligonucleotide of sequence SEQ ID NO: 4 (5'CCG-ACT-GTT-GGC-GCT-GGG3'), the 5' end of which is modified by the $NH_2C_6$— group for the implementation of the covalent bond with ferrocene.

Within the context of the experiments for the detection of the hepatitis C virus, the oligonucleotide probe targeting the virus contains an oligonucleotide of sequence SEQ ID NO: 5 (5'TCA ACT TCG GGA ATC TCA ATG TTA G3'), the 5' end of which is modified by the $NH_2C_6$— group for the implementation of the covalent bond with ferrocene.

Within the context of the experiment for the detection of Ochratoxin (OTA), the probe targeting the toxin is a probe of the aptamer type of sequence SEQ ID NO: 6 (5'GAT CGG GTG TGG GTG GCG TAA AGG GAG CAT CGG ACA3'), the 5' end of which is modified by the $NH_2C_6$— group for the implementation of the covalent bond with ferrocene.

Measurement Techniques

Cyclic Voltammetry (CV)

The analyses are carried out in 0.1 M of KCl with the 5 mM $[Fe(CN)_6]^{4-}$/5 mM $[Fe(CN)_6]^{3-}$ pair in a range of potentials from −0.2 to 0.5 V with a scan rate of 50 mV.s$^{-1}$.

Impedance Spectrometry (EIS)

The analyses are carried out in 0.1 M of KCl with the 5 mM $[Fe(CN)_6]^{4-}$/5 mM $[Fe(CN)_6]^{3-}$ pair. All the impedances are obtained at 0.2 V vs. Ag/AgCl at a DC potential of 10 mV with a range of frequencies from 100 KHz to 0.1 Hz.

Squarewave Voltammetry (SWV)

The analyses are carried out in PBS pH=7.4 containing 10 mM of $Na_2HPO_4$, 1.8 mM of $KH_2PO_4$, 2.7 mM of KCl and 137 mM of NaCl filtered by 0.22 μm membranes and stored at 4° C. until use. SWV analyses are carried out in a range of potentials from −0.3 to 0.4 with a conditioning time of 180 s, frequency 25 Hz and modulation amplitude of 20 mV.

Differential Pulse Voltammetry (DPV)

The analyses are carried out in PBS pH=7.4 containing 10 mM of $Na_2HPO_4$, 1.8 mM of $KH_2PO_4$, 2.7 mM of KCl and 137 mM of NaCl filtered by 0.22 μm membranes and stored at 4° C. until use. The DPV analyses are carried out in a range of potentials from 0.3 to 0.4V at a scan rate of 50 mV.s$^{-1}$ with a pulse height of 45 mV and 0.05 s pulse length.

Example 1

Detection System Containing G4 PAMAM

Modification of the Surface of the Glassy Carbon Electrode with the G4 PAMAM Dendrimers The covalent bonds of the G4 PAMAM dendrimers on the glassy carbon electrode are produced in water containing 0.5 M of $LiClO_4$ by the CV method by scanning the potential from 0.0 to 1.1 V vs. Ag/AgCl as reference electrode during a cycle with a scan rate of 50 mV.s$^{-1}$. During the reaction, the working electrode and the counter electrode are separated in low-volume cells (BASi) containing 200 μl of a 50 μM solution of G4 PAMAM. After fixation of the molecules on the surface and careful washing of the electrodes with double-distilled water, the CV and EIS analyses are carried out.

Association of the Ferrocene Redox Molecule and the Modified Oligonucleotide of Sequence SEQ ID NO: 1.

The ferrocene modified by two phthalimidyl $Fc(NHP)_2$ groups is associated with the dendrimers, the surface of which is modified. The reaction takes place by immersion of the electrode in a 1 mM solution of ferrocene in acetonitrile for 1 hour at ambient temperature. The non-bound residues are washed with acetonitrile and double-distilled water. The electrode is then immersed in a 10 μM solution of modified ssDNA-$C_6NH_2$ probes of SEQ ID NO: 1 prepared in PBS for 1 hour at ambient temperature. The electrode is then rinsed in distilled water and PBS, and in order to saturate the ferrocene phthalimide esters, it is immersed in a 1 mM solution of ethanolamine in PBS solution for 30 min at ambient temperature. The detection system is then washed with distilled water and PBS, then stored in PBS at 4° C. until use. After each step of construction of the DNA detection system, the surface modifications are tested by the SWV method.

Hybridization with the Complementary Oligonucleotide of SEQ ID NO: 2.

Hybridization of the 15 bases complementary to the ssDNA probe of SEQ ID NO: 1 associated on the surface is carried out by immersion of the electrode in the synthetic DNA solution (SEQ ID NO: 2) for 1 hour at 40° C. The different concentrations used for the hybridization are 100 fM, 1 pM, 10 pM, 100 pM, 1 nM, 10 nM and 100 nM. After each incubation, the electrode is carefully washed with distilled water and PBS, then the electrode is analyzed by the SWV method. The control test is carried out by immersion of the electrode in 1 μM of non-complementary oligonucleotide (SEQ ID NO: 3) in PBS and incubation under the same conditions as for the synthetic DNA molecule of interest (SEQ ID NO: 2) (1 hour at 40° C.). The same conditions are applied for detecting the samples originating from PCR, which are treated beforehand at 90° C. for 5 min for dehybridization of the double-strand DNA obtained after PCR.

Results a) Detection of the Synthetic DNA Molecule of Interest of Sequence SEQ ID NO: 2

Figure 3A:
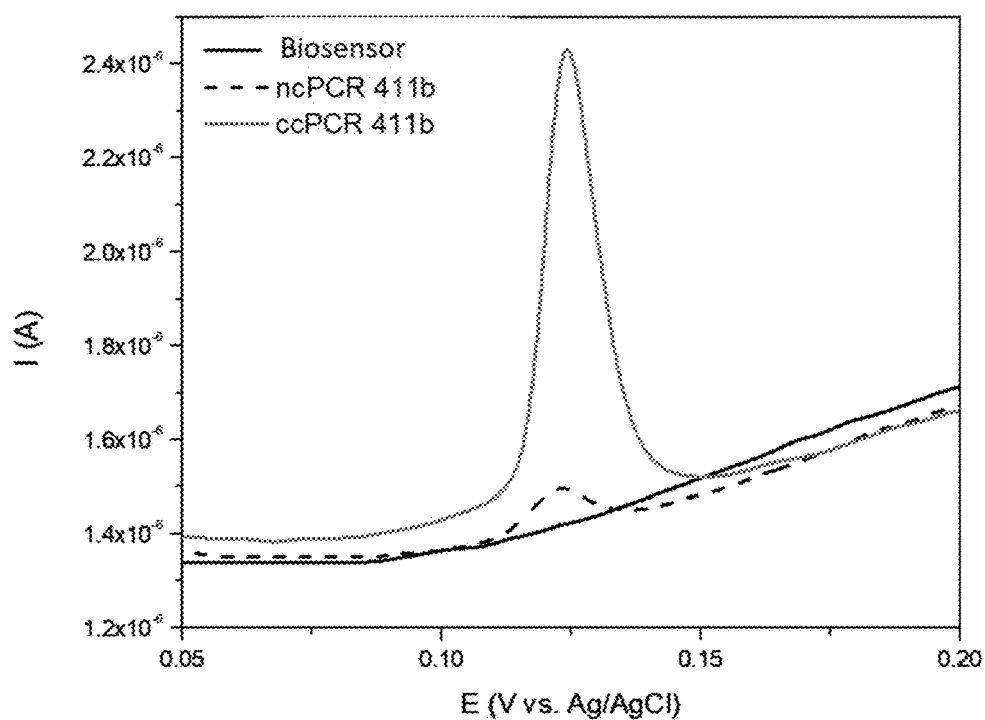
FIGS. 3a and 3b show the specificity of the detection system according to the invention when the nanomaterial used is the G4 PAMAM.
Figure 3B:
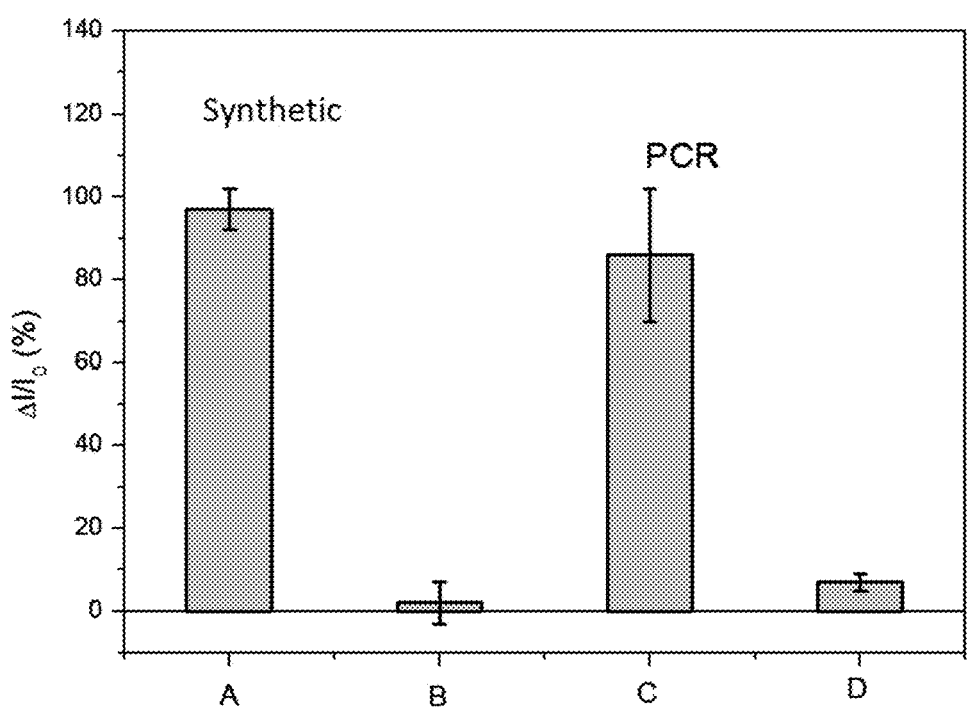
Figure 3C:
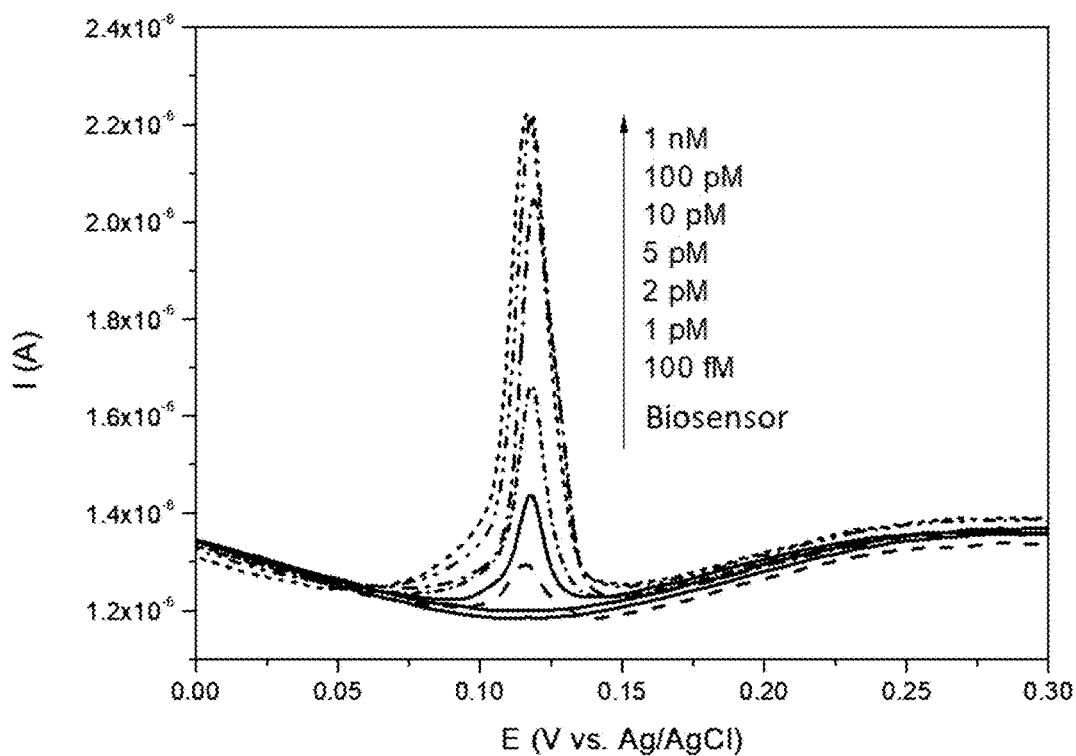
FIG. 3c shows the range of concentrations that can be detected by said system.

Detection of the synthetic DNA molecule of interest of sequence SEQ ID NO: 2 is carried out by the SWV method. The detection system is successively incubated in a solution containing concentrations of DNA varying between 100 fM and 1 nM and an analysis by SWV is carried out for each concentration. FIG. 3c shows the increase in the current corresponding to the ferrocene at 0.11V with each concentration of DNA of interest. This variation in the current is proportional to the concentration of the synthetic DNA molecule of interest.

The first positive signal during the detection of DNA molecule of interest is obtained after incubation of the detection system in a 1 pM solution of DNA of interest and leads to a current variation of 10%. And, the saturation of the detection system is observed at 100 pM with a current variation of 97%, which corresponds to the changes in the redox signal of the ferrocene.

The increase in the current during the detection of the DNA molecule of interest is explained by the unmasking of the redox molecule by hybridization of the synthetic complementary DNA molecule of interest (SEQ ID NO: 2) with the oligonucleotide probe SEQ ID NO: 1 and by the use of G4 PAMAM. This change in the orientation of the probe ssDNA/synthetic complementary DNA molecule of interest, complex or originating from PCR samples, causes the increase in the transfer of electrons between the ferrocene and the G4 PAMAM (FIGS. 3a and 3c).

b) Detection of the DNA Molecule of Interest Originating from PCR

The detection system comprising G4 PAMAM and the oligonucleotide probe of sequence SEQ ID NO: 4 is prepared according to the methods described above for detecting the DNA molecule of interest composed of 411 bases originating from PCR (cPCR).

After incubation, the current variation corresponding to the ferrocene is calculated. The value of the variation obtained by 5 independent experiments is 86%. When the sample does not contain the product ncPCR the sequence of which differs from that of cPCR by one nucleotide acid, the current variation is not more than 7% (FIG. 3a and FIG. 3b). These results show that said system can efficiently and specifically detect a DNA molecule of interest such as that of *Mycobacterium tuberculosis* and differentiate the strains resistant to rifampicin. It can be used in the clinical field.

Example 2

Detection System Containing Gold Nanoparticles

Modification of the Gold Nanoparticles and Their Association on the Surface 2 g (0.008 mol) of cystamine dichlorhydrate is dissolved in 20 ml of 5M NaOH (0.1 M) and extracted with 10 ml of $CH_2Cl_2$. The organic phase is rinsed with 10 ml of distilled water, dried over $MgSO_4$ and concentrated under vacuum. Cystamine dissolved in double-distilled water is added to the solution of 1 ml gold nanoparticles (OD=0.4) for a final concentration of 50 µM. The solution is incubated at 4° C. until use. The cystamine concentration as well as the incubation time were optimized to make it possible to obtain wells of modified, non-aggregated gold nanoparticles for analysis by ultraviolet-visible spectrometry and dynamic light scattering.

After this reaction, the sample of gold nanoparticles modified with cystamine ($AuNPs-NH_2$) is centrifuged for 20 min at 14,000 rpm in order to remove the cystamine residues. The pellet is then rinsed twice with 1 ml of double-distilled water and centrifuged until the excess of cystamine is eliminated. Finally, the $AuNPs-NH_2$ sample is dissolved in 300 µl of water.

100 µl of $AuNPs-NH_2$ is mixed with a 100 µl solution of N-(3-dimethylaminopropyl)-N'-ethylcarbodiimide hydrochloride/N-Hydroxysuccinimide (10 mM/10 mM dissolved in water) so as to associate the $AuNPs-NH_2$ to the glassy carbon electrode. Then, the electrode modified with carboxylic —COOH groups is immersed in this mixture and is incubated for 2 hours at ambient temperature. Different incubation times were tested and 2 hours is the optimum duration for a good performance of the detection system. The electrode is carefully rinsed with double-distilled water, then analyzed by EIS measurements.

Modification of AuNPs by the cystamine is optimized and monitored by ultraviolet-visible spectrometry. The AuNPs of 5 nm diameter absorb visible ultraviolet at 520 nm, while the absorption value of the modified AuNPs is increased and thus confirms the effectiveness of the reaction.

Electrodeposition of β-Alanine and Ethanolamine

The covalent bond of the β-alanine on the glassy carbon electrode is produced in water containing 0.5 M of $LiClO_4$ by scanning potentials from 0.2 to 1.1 V vs. Ag/AgCl as reference electrode for 10 cycles until saturation with a scan rate of 50 $mV.s^{-1}$. During the reaction, the working electrode and the counter electrode are separated in low-volume cells (BASi) containing 200 µl of a 10 mM solution of β-alanine. Then the electrode is carefully rinsed with double-distilled water. Saturation of the surface by ethanolamine is carried out under the same conditions, by scanning potentials from 0.2 to 1.1 V vs. Ag/AgCl for 3 cycles. The concentration of ethanolamine used for this reaction is 1 mM prepared in water containing 0.5 M of $LiClO_4$. After fixation of the molecules on the surface and careful rinsing of the electrode with double-distilled water, the EIS analyses are carried out.

Construction of the Detection System

The ferrocene modified by two phthalimidyl $Fc(NHP)_2$ groups is associated on the modified $AuNPs-NH_2$ surface. The reaction is carried out by immersion of the electrode in a 1 mM solution of ferrocene in acetonitrile for 1 hour at ambient temperature. The non-bound residues are washed with acetonitrile and double-distilled water. Then the electrode is immersed in a 10 µM solution of modified DNA SEQ ID NO: 1 prepared in PBS for 1 hour at ambient temperature. After rinsing the electrode in distilled water and PBS, the electrode is immersed in a 1 mM solution of ethanolamine in PBS for 30 min at ambient temperature so as to saturate the ferrocene phthalimide esters. The detection system is then washed with distilled water and PBS, then stored in PBS at 4° C. until use. After each step of construction of the DNA probe, the surface modifications are monitored by the EIS method.

Hybridization with Synthetic Complementary DNA Molecule of Interest

Hybridization of the synthetic complementary DNA molecule of interest to the ssDNA probe associated on the surface is carried out by immersion of the electrode in the solution of synthetic DNA molecule of interest of SEQ ID NO: 2 for 1 hour at 40° C. The different concentrations used for the hybridization are 100 fM, 1 pM, 10 pM, 100 pM, 1 nM, 10 nM and 100 nM. After each incubation, the electrode is carefully washed with distilled water and PBS, then the electrode is analyzed by the DPV method.

The PCR products contain 411 bases and are detected by a detection system containing the PCR probe of SEQ ID NO: 4 in a solution according to the same method described above.

The control test is carried out by immersion of the electrode in 1 µM of non-complementary target in PBS and incubated under the same conditions as for the complementary synthetic DNA molecule of interest (1 hour at 40° C.). The same conditions are applied for detecting the samples originating from PCR.

Results a) Detection of the Synthetic DNA Molecule of Interest of Sequence SEQ ID NO: 2

Detection of the DNA molecule of interest is carried out by the SWV method. The detection system is successively incubated in a solution containing concentrations of DNA varying between 100 fM and 1 nM and an analysis by SWV is carried out for each concentration. FIG. 4c shows the increase in the current corresponding to ferrocene at 0.11V with each concentration of complementary DNA of interest. This variation in the current is proportional to the concentration of synthetic DNA molecule of interest (SEQ ID NO: 2).

The first positive signal during the detection of synthetic DNA molecule of interest is obtained after incubation of the detection system in a solution containing 100 fM of synthetic DNA molecule of interest and leads to a current variation of 10%.

And, saturation of the detection system is observed at 100 pM with a current variation of 97%, which corresponds to the changes of ferrocene. Nevertheless, analyses at concentrations of 100 pM to 1 nM can be carried out with the detection system used (FIG. 4c).

b) The Same Detection System as that Mentioned in Example 2a) is Constructed with Oligonucleotide Probes of SEQ ID NO: 4 in Order to Detect a Sample Comprising the PCR Product Corresponding to the Mutated rpoB Gene (cPCR) of *Mycobacterium Tuberculosis*.

Figure 4A:
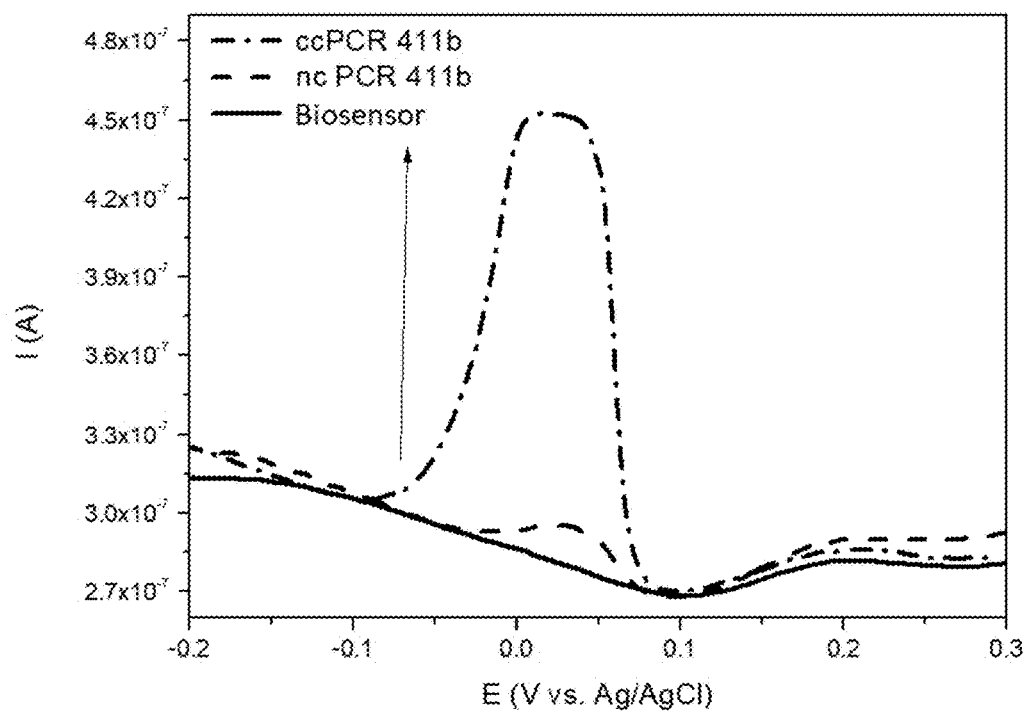
FIGS. 4a and 4b show the specificity of the detection system according to the invention when the nanomaterial used is modified gold nanoparticles.
Figure 4B:
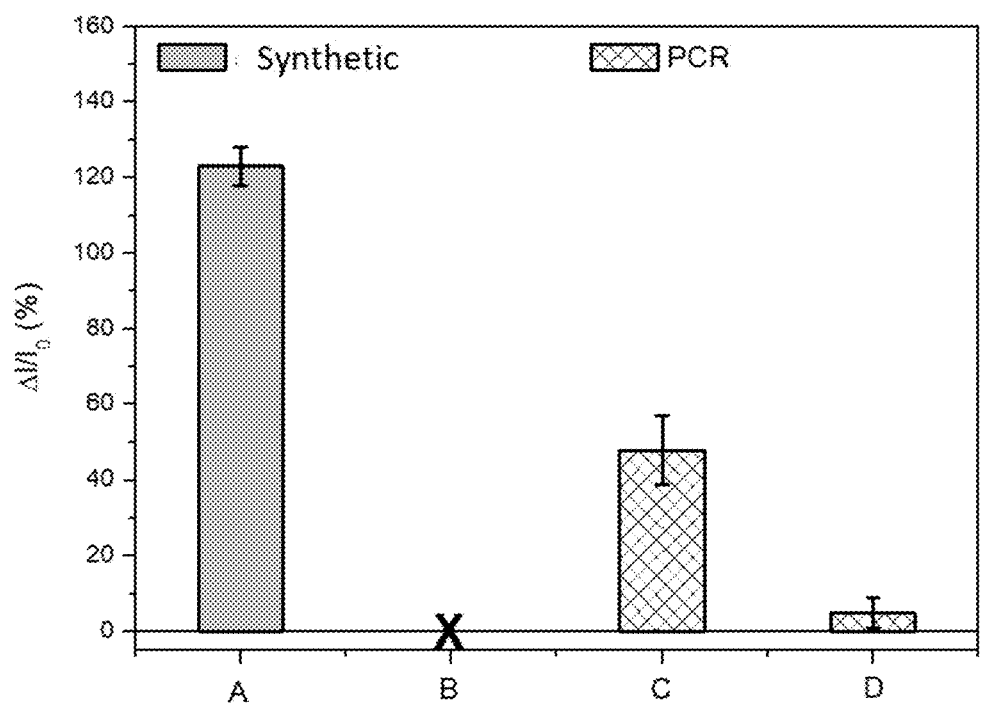
Figure 4C:
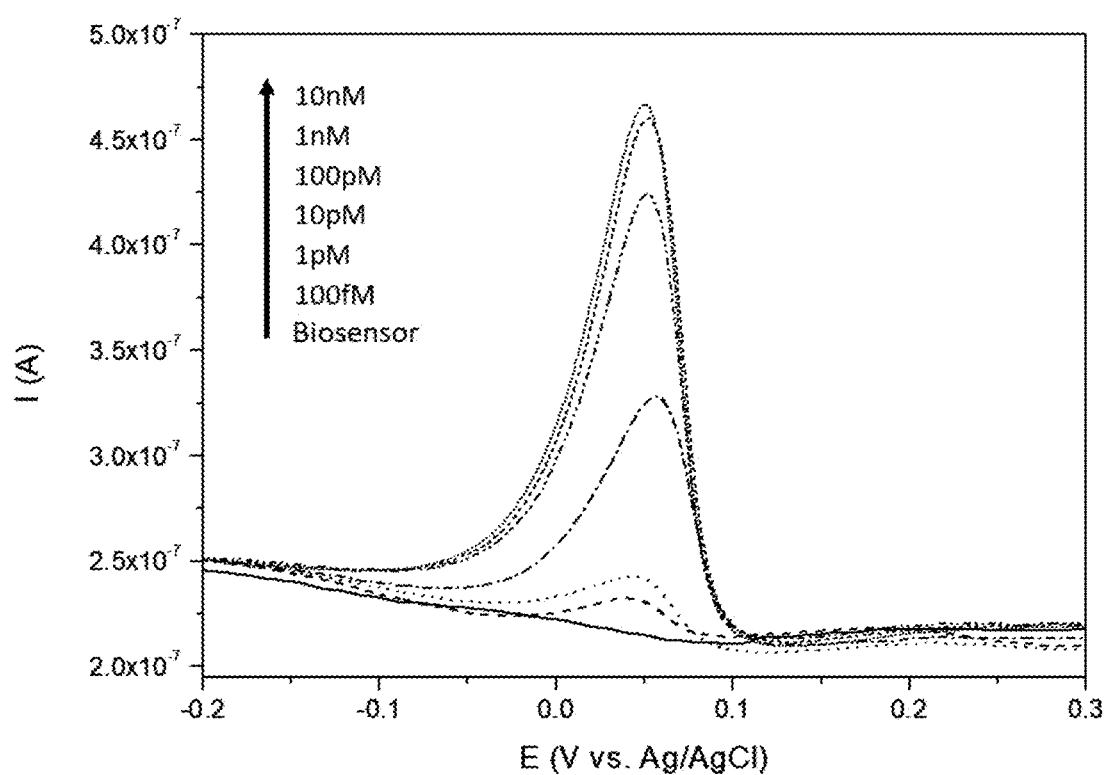
FIG. 4c shows the range of concentrations that can be detected by said system.

Said detection system is capable of producing a specific electrical signal when the cPCR product is present in the sample (FIGS. 4a and 4b). Said system makes it possible to specifically detect the strains of *Mycobacterium tuberculosis* that are resistant to rifampicin.

Example 3

Detection System Containing Gold Nanoparticles and G4 PAMAM (G4-AuNPs)

Modification of the Surface of the Glassy Carbon Electrode with the G4 PAMAM Dendrimers The covalent bonds of the G4 PAMAM dendrimers on the glassy carbon electrode are produced in water containing 0.5 M of $LiClO_4$ by the CV method by scanning the potential from 0.0 to 1.1 V vs. Ag/AgCl as reference electrode during a cycle with a scan rate of 50 $mV.s^{-1}$. During the reaction, the working electrode and the counter electrode are separated in low-volume cells (BASi) containing 200 μl of a 50 μM solution of G4 PAMAM. After fixation of the molecules on the surface and careful washing of the electrodes with double-distilled water, CV and EIS analyses are carried out.

Modification of the Surface of the Glassy Carbon Electrode with the G4 PAMAM Dendrimers and the AuNPs.

The first step in the construction of the detection system is the electrodeposition of the G4 PAMAM dendrimers on the surface of the glassy carbon electrode. The electrodeposition is carried out by the CV technique by scanning the potential from 0.0 to 1.1 V vs. Ag/AgCl as reference electrode during a cycle with a scan rate of 50 $mV.s^{-1}$. During the oxidation reaction, the amine groups of the dendrimers form a —$NH.^+$ cationic radical which interacts with the C=C aromatic groups of the carbon-containing surface.

Modification of the Gold Nanoparticles and Their Association on the Surface 2 g (0.013 mol) of cystamine dihydrochloride is dissolved in 20 ml of 5 M NaOH (0.1 M) and extracted with 10 ml of $CH_2Cl_2$. The organic layer is rinsed with 10 ml of distilled water, dried over $MgSO_4$ and concentrated under vacuum. Cystamine dissolved in double-distilled water is added to the solution of 1 ml of gold nanoparticles (OD=0.4) for a final concentration of 50 μM. The solution is incubated at 4° C. until use.

After this reaction, the sample of gold nanoparticles modified with cystamine ($AuNPs-NH_2$) is centrifuged for 20 min at 14,000 rpm in order to remove the cystamine residues. The pellet is then rinsed twice with 1 ml of double-distilled water and centrifuged until the excess cystamine is removed. Finally, the sample of $AuNPs-NH_2$ is dissolved in 300 μl of water.

Association of the AuNPs and the G4 PAMAM Dendrimers

In order to associate the $AuNPs-NH_2$ to the glassy carbon electrode modified by the G4 PAMAM dendrimers, glutaraldehyde is used as a link. The electrode modified by the G4 PAMAM dendrimers is immersed in a solution of 0.5% glutaraldehyde for 20 min, then carefully rinsed. Then, the electrode is incubated in 100 μl of $AuNPs-NH_2$ for 2 hours at ambient temperature. Different incubation times were tested and 2 hours is the optimum duration for a good performance of the detection system. The electrode is carefully rinsed with double-distilled water and is then analyzed by CV and EIS measurements.

Association of the Ferrocene Redox Molecule and the ssDNA Probe

The ferrocene modified by two phthalimidyl $Fc(NHP)_2$ groups is associated with the $AuNPs-NH_2$, the surface of which is modified. The reaction takes place by immersion of the electrode in a solution of 1 mM of ferrocene in acetonitrile for 1 hour at ambient temperature. The non-bound residues are washed with acetonitrile and double-distilled water. Then the electrode is immersed in a 10 μM solution of $ssDNA-C_6NH_2$ probes prepared in PBS for 1 hour at ambient temperature. The electrode is then rinsed in distilled water and PBS and immersed for 30 min at ambient temperature in a solution of 1 mM ethanolamine in PBS solution so as to saturate the ferrocene phthalimide esters. The detection system is then washed with distilled water and PBS, then stored in PBS at 4° C. until use. After each step of construction of the DNA detection system, the surface modifications are monitored by the SWV method.

Hybridization with the Synthetic DNA Molecule of Interest of Sequence SEQ ID NO: 2

Hybridization of the synthetic DNA molecule of interest (SEQ ID NO: 2) to the ssDNA probe SEQ ID NO: 1 associated on the surface is carried out by immersion of the electrode in the solution of synthetic DNA molecule of interest for 1 hour at 40° C. The different concentrations used for the hybridization are 100 fM, 1 pM, 10 pM, 100 pM, 1 nM, 10 nM and 100 nM. After each incubation, the electrode is carefully washed with distilled water and PBS, then the electrode is analyzed by the SWV method. The control test is carried out by immersion of the electrode in 1 μM of non-complementary DNA molecule of interest of sequence SEQ ID NO: 3 in PBS and incubated under the same conditions as for the DNA molecule of interest (1 hour at 40° C.). The same conditions are applied for detecting the samples originating from PCR.

Results a) Detection of the Synthetic DNA Molecule of Interest

Detection of the DNA molecule of interest SEQ ID NO: 2 is carried out by the SWV method. The detection system is successively incubated in a solution containing concentrations of DNA varying between 100 fM and 1 nM and an analysis by SWV is carried out for each concentration. FIG. 5c shows the increase in the current corresponding to ferrocene at 0.11V with each concentration of synthetic DNA molecule of interest SEQ ID NO: 2. This variation in the current is proportional to the concentration of the synthetic DNA molecule of interest.

The first positive signal during the detection of DNA molecule of interest SEQ ID NO: 2 is obtained after incubation of the detection system in a solution of DNA molecule of interest SEQ ID NO: 2 of 1 pM and leads to a current variation of 10%.

And, saturation of the detection system is observed at 100 pM with a current variation of 97%, which corresponds to the changes of the ferrocene. However, analyses at concentrations of 100 pM to 1 nM are feasible with the detection system used (FIG. 5c).

b) The Same Detection System as that Mentioned in Example 2 is Constructed with Oligonucleotide Probes of SEQ ID NO: 4 in Order to Detect a Sample Comprising the PCR Product Corresponding to the Mutated rpoB Gene (cPCR) of *Mycobacterium Tuberculosis*.

Figure 5A:
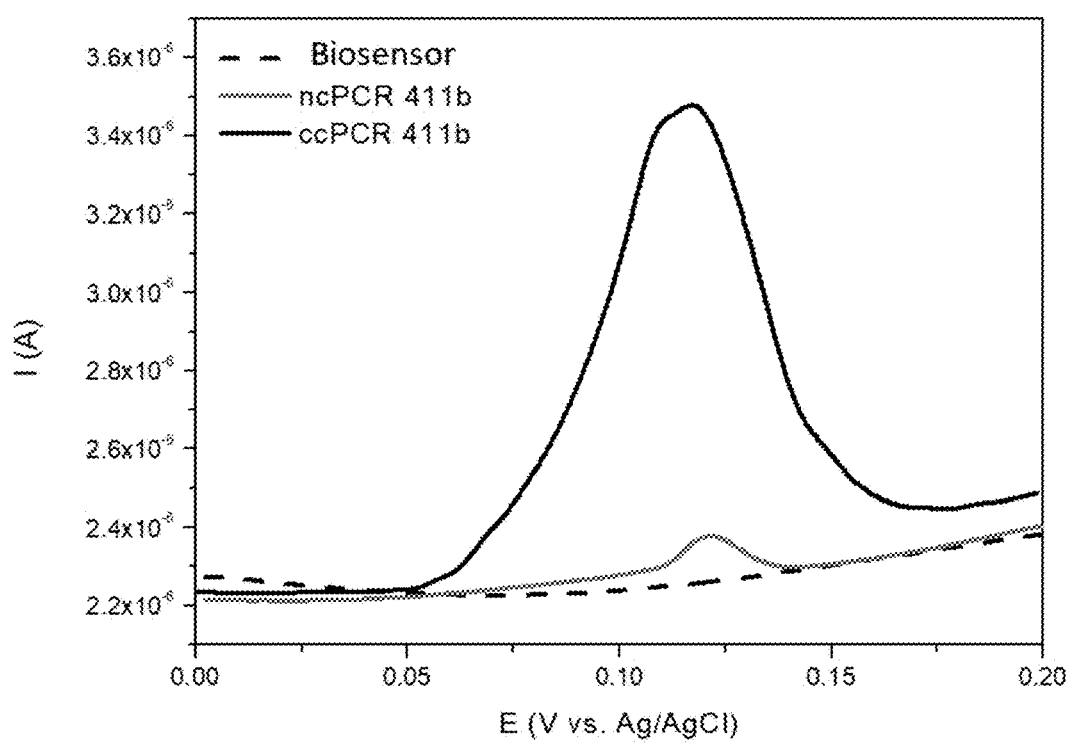
FIGS. 5a and 5b show the specificity of the detection system according to the invention when the nanomaterial used is G4 PAMAM bound with modified gold nanoparticles.
Figure 5B:
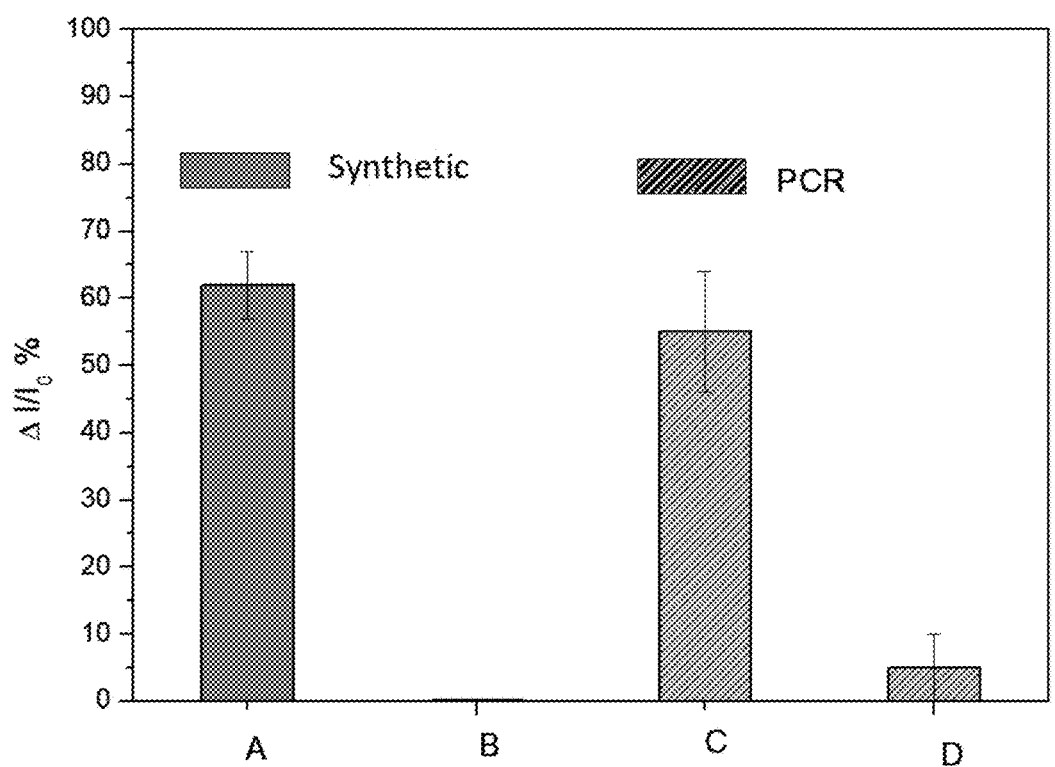
Figure 5C:
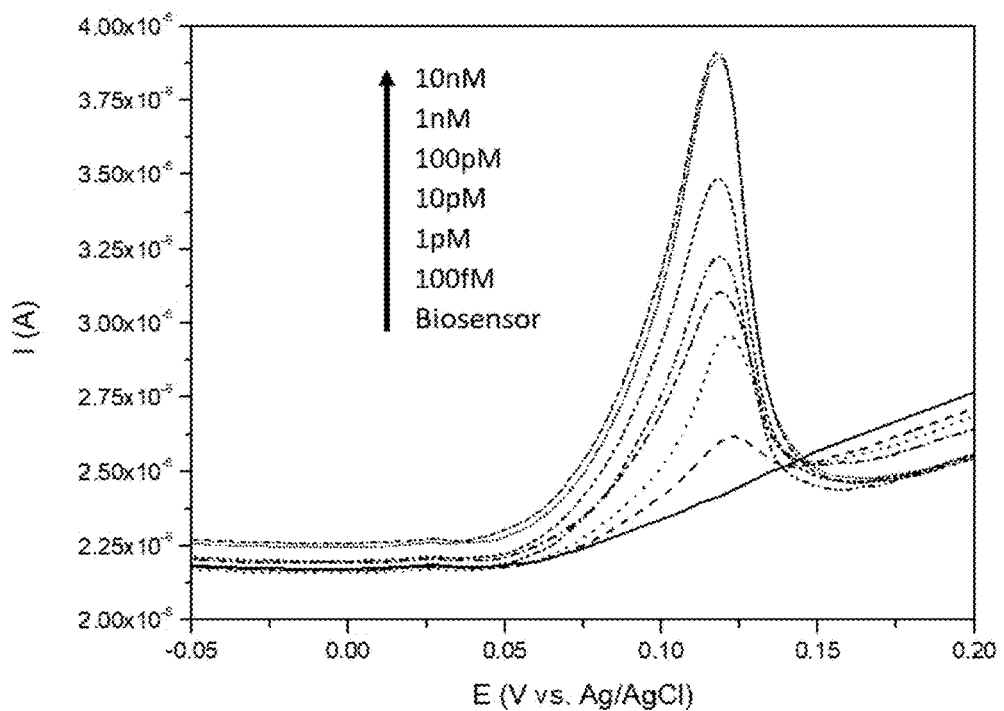
FIG. 5c shows the range of concentrations that can be detected by said system.

Said detection system is capable of producing a specific electrical signal when the cPCR product is present in the sample (FIGS. 5a and 5b).

c) The Same Detection System as that Mentioned in Example 3a) is Constructed with Oligonucleotide Probes of Sequence SEQ ID NO: 5 in Order to Detect a Sample of Synthetic DNA of the Hepatitis C Virus.

Figure 6:
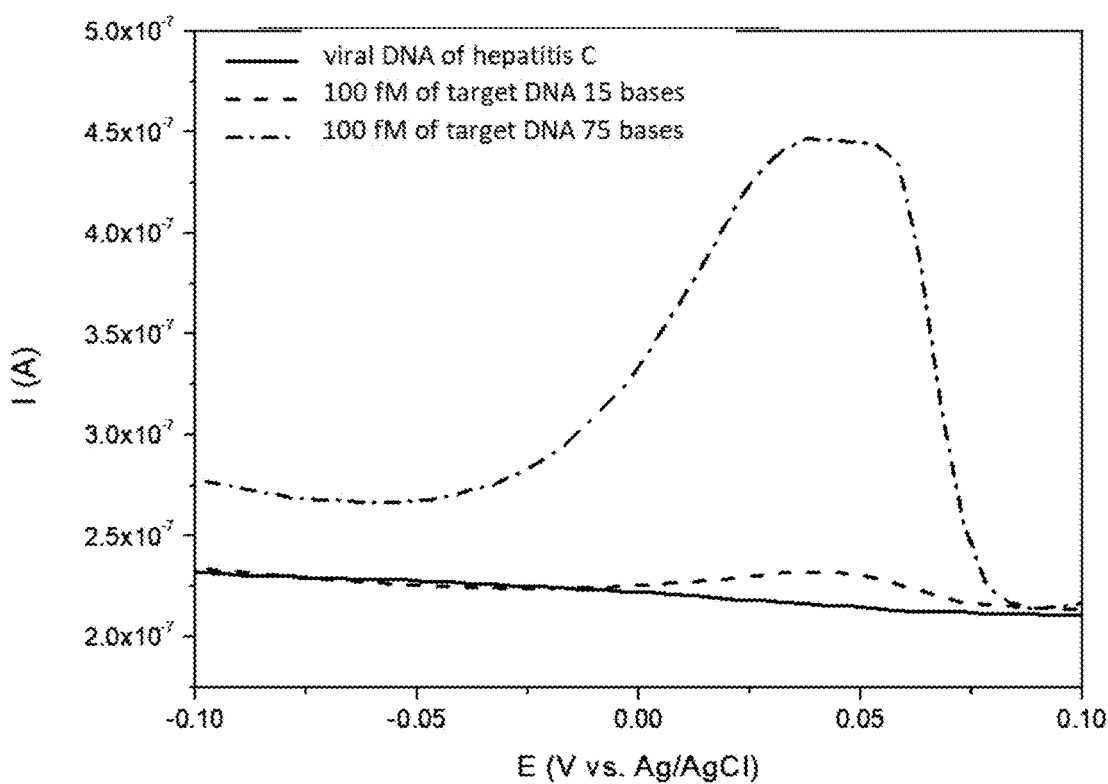

Said detection system is capable of producing an electrical signal in the presence of the synthetic DNA molecule (FIG. 6). Said system thus makes it possible to detect the hepatitis C virus.

The table I below summarizes the detection ranges obtained according to the aforementioned different examples:

TABLE I

| Detection system | Dynamic range | Linear range | Quantitative limit |
|---|---|---|---|
| PAMAM | 1 pM-100 pM | 1 pM-10 pM | 1 pM |
| AuNPs | 100 fM-1 nM | 1 pM-1 nM | 100 fM |
| PAMAM-AuNPs | 100 fM-10 nM | 100 fM-10 nM | 100 fM |

Example 4

Detection of Ochratoxin A (OTA) with a Detection System Comprising G4 PAMAM

The same detection system as that mentioned in Example 1 is constructed with an aptamer probe of sequence SEQ ID NO: 6 in order to detect the presence or absence of OTA in a food sample such as milk or wine, the matrix of which is complex.

Figure 7A:
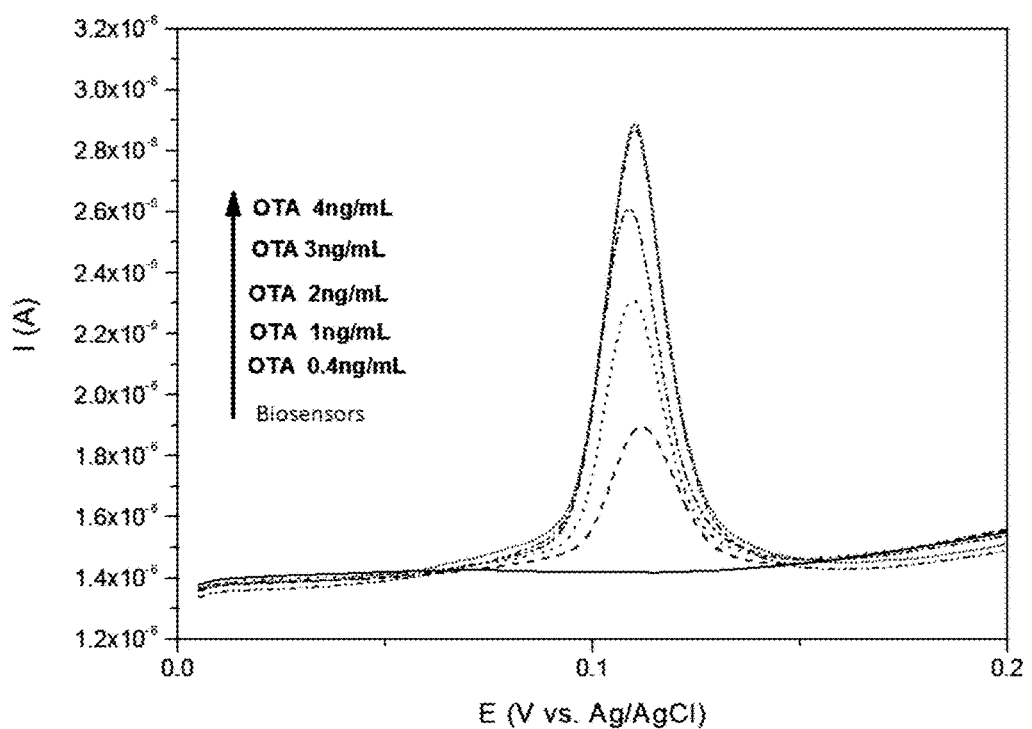
FIGS. 7a and 7b show the specificity of the detection system according to the invention when the oligonucleotide probe is an aptamer specific to Ochratoxin A. In particular.
Figure 7B:
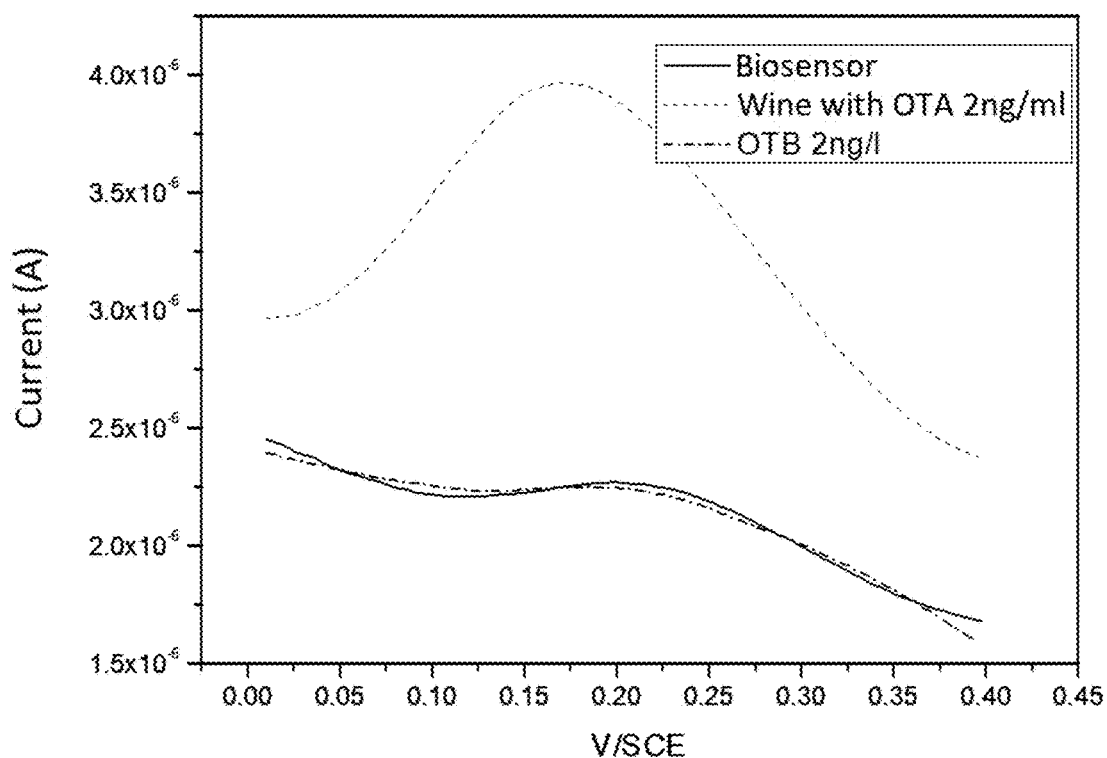

Said detection system is capable of producing an electrical signal in the presence of OTA (FIGS. 7a and 7b). Said system thus allows the detection of the OTA toxin. The presence of another aptamer non-specific toxin such as OTB which is not detected (FIG. 7b).

Example 5

Detection of OTA with a Detection System Containing G2 PAMAM

Modification of the Surface of the Glassy Carbon Electrode with the G2 PAMAM Dendrimers The covalent bonds of the G2 PAMAM dendrimers on the glassy carbon electrode are produced in water containing 0.5 M of $LiClO_4$ by the CV method by scanning the potential from 0.0 to +1.1 V vs. Ag/AgCl as reference electrode during a cycle with a scan rate of 50 $mV.s^{-1}$. During the reaction, the working electrode and the counter electrode are separated in low-volume cells (BASi) containing 200 µl of a solution of G2 PAMAM of 50 µM. After fixation of the molecules on the surface and careful washing of the electrodes with double-distilled water, CV and EIS analyses are carried out.

Association of the Naphthoquinone Redox Molecule and the G2 PAMAM

The naphthoquinone modified by propanoic acid is associated with the dendrimers. The reaction takes place by peptide coupling between the propanoic acid and the amine functions on the surface of the dendrimer using 1-Ethyl-3-(3-dimethylaminopropyl)carbodiimide (EDC) as coupling agent.

In order to verify good grafting of the redox molecules to the surface of the dendrimers, the signal is analyzed and shows an intense peak in the potential of the redox molecule (−0.22V) immobilized on the surface.

Figure 8:
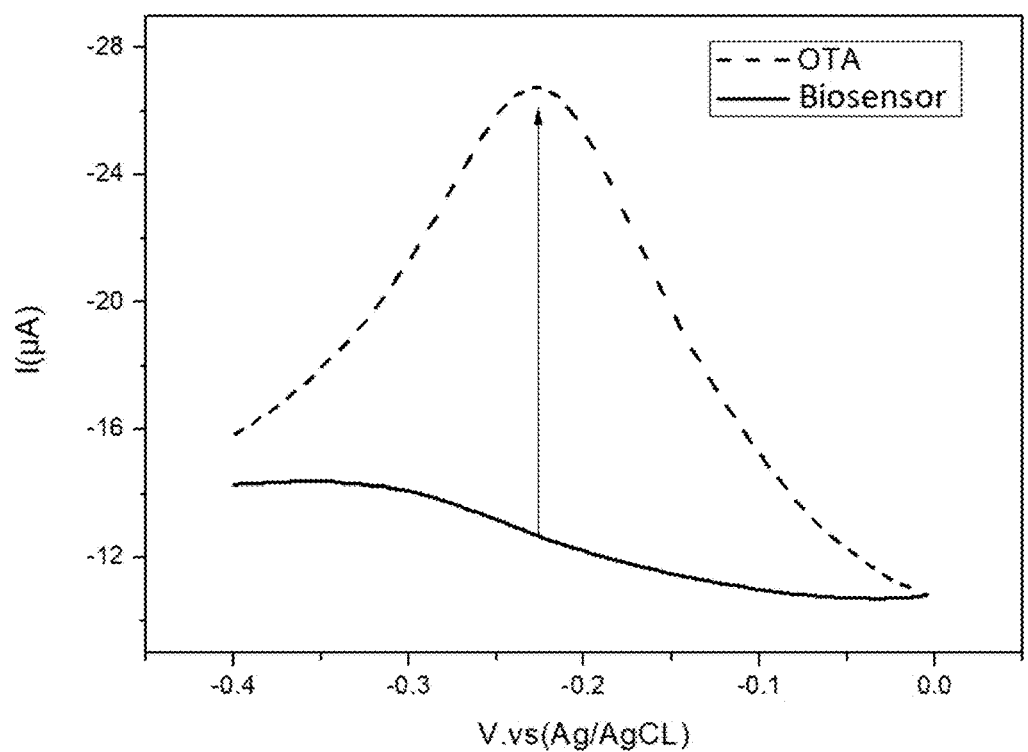

Association of the Modified Oligonucleotide Probe of Sequence SEQ ID NO: 6 and G2 PAMAM The electrode is incubated in an aptamer DNA solution specific to OTA modified by a COOH group in its 5' end position. The aptamer is covalently grafted to the surface of the dendrimer by peptide coupling between the surface amine and the acid function in position 5' of the aptamer; the duration of this reaction is 1 hour. The surface is washed, then stabilized in a PBS buffer solution and the signal is measured (FIG. 8).

In order to verify good grafting of the oligonucleotide probes of SEQ ID NO: 6 in the form of aptamer to the surface of the dendrimers, the signal emitted by the redox molecule is analyzed and shows significant reduction in the potential of the redox molecule (−0.22V) immobilized on the surface.

Bringing OTA into Contact with the Detection System Containing G2 PAMAM

The OTA is brought into contact with the detection system as prepared for 1 hour, then the surface is washed.

Results

The detection system described above is used in order to detect the presence or absence of OTA in a food sample such as milk or wine, the matrix of which is complex.

Analysis of the naphthoquinone signal (FIG. 8) indicates an increase in the signal at the potential of −0.22V, this being due to the unmasking of the redox molecule caused by the complementary bond between the OTA and its complementary aptamer of SEQ ID NO: 6.

In other words, said detection system containing G2 PAMAM is capable of producing an electrical signal in the presence of the OTA toxin.

Example 6

Detection of OTA with a Detection System Comprising Magnetic Nanoparticles

The same detection system as that mentioned in Example 5 is constructed with magnetic nanoparticles modified by chitosan as nanomaterial in order to detect the presence or absence of OTA in a food sample such as milk or wine, the matrix of which is complex.

The magnetic nanoparticles are magnetic nanoparticles of iron oxide ($Fe_3O_4$) of size 10 nm-100 nm and are obtained with a conventional synthesis, then modified by chitosan in order to render them cationic.

Figure 9:
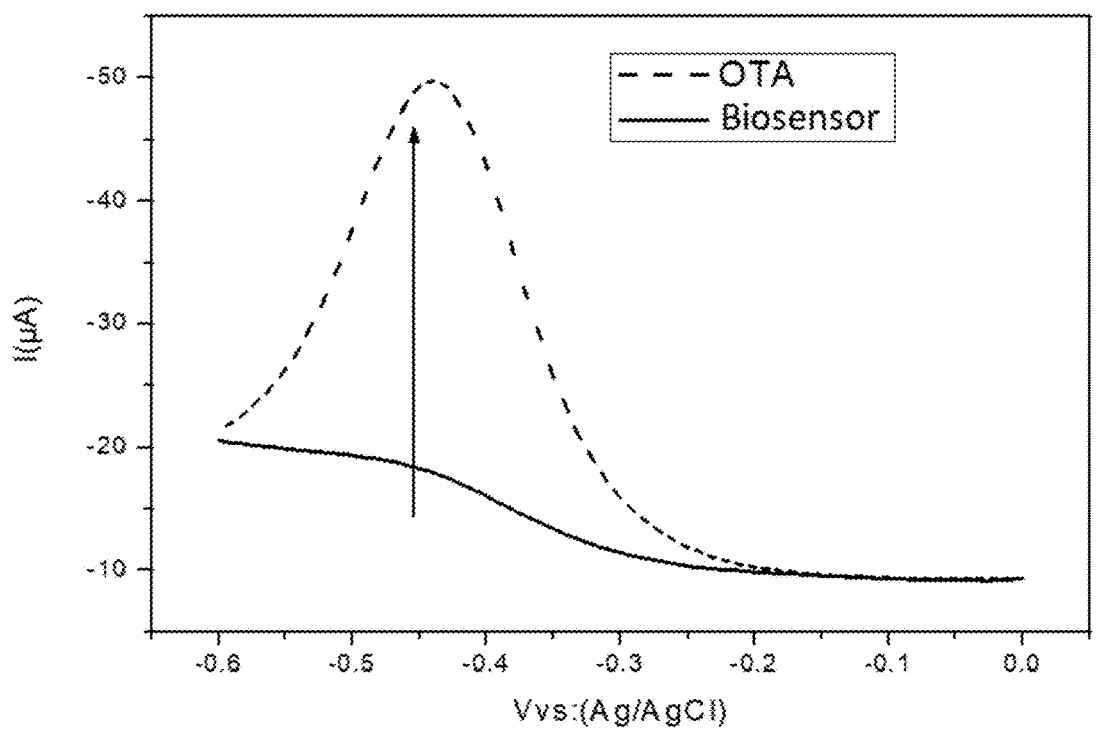

Analysis of the naphthoquinone signal (FIG. 9) indicates an increase in the signal at the potential of −0.4V, this being due to the unmasking of the redox molecule caused by the complementary bond between the OTA and its complementary aptamer of SEQ ID NO: 6.

In other words, said detection system containing magnetic nanoparticles modified with chitosan is capable of producing an electrical signal in the presence of the OTA toxin.

Example 7

Detection of OTA with a Detection System Containing Nanoparticles of Chitosan

The same detection system as that mentioned in Example 6 is constructed with microspheres of chitosan as nanomaterial in order to detect the presence or absence of OTA in a food sample such as milk or wine, the matrix of which is complex.

Figure 10:
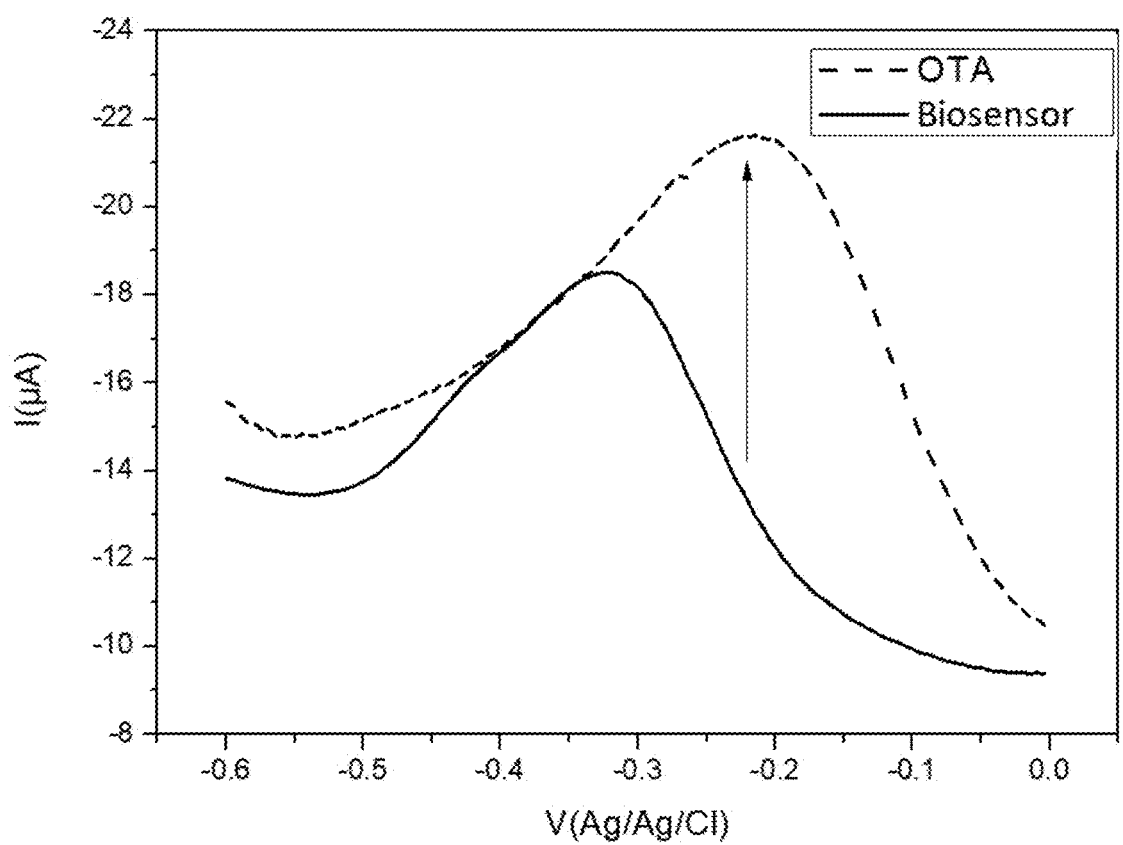

Analysis of the naphthoquinone signal (FIG. 10) indicates an increase in the signal at the potential of −0.22V, this being due to the unmasking of the redox molecule caused by the complementary bond between the OTA and its complementary aptamer of SEQ ID NO: 6.

In other words, said detection system containing microspheres of chitosan is capable of producing an electrical signal in the presence of the OTA toxin, despite a variation in the signal that is less significant than previously.

However, optimization of the size of these microspheres of chitosan would allow a greater variation in the signal.

The invention claimed is:

1. A system for electrochemical detection of molecules of interest, said system comprises:
- a conductive material providing a regular surface for attaching a nanomaterial;
- at least one nanomaterial bearing positive functions, covalently bound to said conductive material;
- at least one redox molecule; and
- at least one single-stranded oligonucleotide probe targeting a molecule of interest,
- said redox molecule being covalently bound to said nanomaterial;
- said oligonucleotide probe being covalently bound to said nanomaterial or to the redox molecule; and
- the number of positive functions of said nanomaterial being greater than the number of oligonucleotide probes.

2. The electrochemical detection system according to claim 1, characterized in that said redox molecule is covalently bound to both; to said nanomaterial and to the oligonucleotide probe.

3. The electrochemical detection system according to claim 2, characterized in that said system comprises:
- at least two types of redox molecules, wherein the oxidation-reduction potentials of each redox molecule are different; and
- at least two types of single-stranded oligonucleotide probes, each targeting a different molecule of interest, one type of oligonucleotide probes being bound to one single type of redox molecules.

4. An electrochemical method for the detection of at least two types of molecules of interest in a sample, comprising the following steps:
- (i) bringing a detection system as defined in claim 3 into contact with a sample capable of containing said molecules of interest; and
- (ii) measuring the redox signals specific to said molecules of interest.

5. The electrochemical detection system according to claim 1, characterized in that said oligonucleotide probe and said redox molecule are respectively covalently bound to said nanomaterial.

6. The electrochemical detection system according to claim 1, characterized in that said nanomaterial bearing positive functions is selected from the group comprising:
- a dendrimer;
- metal particles;
- magnetic nanoparticles;
- hybrid nanomaterials based on chitosan; and
- conductive polymers, optionally modified by positive functions.

7. The electrochemical detection system according to claim 6, wherein the dendrimer is the dendrimer of the poly(amidoamine) type, chosen from second, fourth or sixth generation.

8. The electrochemical detection system according to claim 1, characterized in that said conductive material is formed from carbon, or a metal.

9. The electrochemical detection system according to claim 8, wherein said conductive material is formed from carbon which is chosen from carbon nanotubes, glassy carbon, graphite, or graphene.

10. The electrochemical detection system according to claim 1, characterized in that said redox molecule is selected from the group comprising ferrocene, quinone, methylene blue, metalloporphyrins, or viologen.

11. The electrochemical detection system according to claim 1, characterized in that the oligonucleotide probes target at least one molecule of interest, said molecule of interest is selected from a DNA molecule, a RNA molecule, a protein or a toxin.

12. A modified support for the preparation of the detection system according to claim 1, said modified support consisting of:
- a conductive material providing a regular surface for attaching a nanomaterial;
- a nanomaterial bearing positive functions; and
- at least one redox molecule, said nanomaterial being situated between said conductive material and said redox molecule and being covalently bound to the latter two.

13. A kit for the preparation of an electrochemical detection system for electrochemical detection of molecules of interest, the system including:
- a conductive material providing a regular surface for attaching a nanomaterial;
- at least one nanomaterial bearing positive functions, covalently bound to said conductive material;
- at least one redox molecule; and
- at least one single-stranded oligonucleotide probe targeting a molecule of interest,
- said redox molecule being covalently bound to said nanomaterial;
- said oligonucleotide probe being covalently bound to said nanomaterial or to the redox molecule;
- the number of positive functions of said nanomaterial being greater than the number of oligonucleotide probes, said kit consisting of:
- (i) a modified support as defined in claim 12, and
- (ii) at least one oligonucleotide targeting a molecule of interest.

14. A method for the preparation of an electrochemical detection system for electrochemical detection of molecules of interest, said system including a conductive material providing a regular surface for attaching a nanomaterial;
- at least one nanomaterial bearing positive functions, covalently bound to said conductive material;
- at least one redox molecule; and
- at least one single-stranded oligonucleotide probe targeting a molecule of interest,
- said redox molecule being covalently bound to said nanomaterial;
- said oligonucleotide probe being covalently bound to said nanomaterial or to the redox molecule;
- the number of positive functions of said nanomaterial being greater than the number of oligonucleotide probes, said method comprising:

(i) bringing a modified support as defined in claim 12 into contact with at least one functionalized oligonucleotide targeting a molecule of interest;

(ii) forming covalent bonds between the aforementioned modified support and said functionalized oligonucleotide.

15. An electrochemical method for the detection of at least one type of molecule of interest in a sample, comprising the following steps:

(i) bringing a detection system as defined in claim 1 into contact with a sample capable of containing said molecule of interest; and (ii) measuring electrochemically the redox signal from the redox molecule upon interaction of said molecule of interest with the single-stranded oligonucleotide probe.

16. The electrochemical detection method according to claim 15, characterized in that it comprises, in addition to steps (i) and (ii) and after step (ii), the quantitative analysis of said molecule of interest, with reference to a calibration curve.

17. A method for identifying resistance to a medicinal product and monitoring the presence of a medicinal product in the biological fluids during in vitro or in vivo diagnosis of a disease, comprising a step of bringing into contact an electrochemical detection system as defined in claim 1 and the biological fluids, detecting said pathogen to identify resistance to a medicinal product or said medicinal product to monitor the presence of a medicinal product in the biological fluids by electrochemical measurement of the redox signal from the redox molecule upon interaction of said pathogen with the single-stranded oligonucleotide probe.

18. A method for detecting the presence of a pathogen or a toxin in an agri-food or pharmaceutical sample or an effluent, comprising a step of bringing into contact an electrochemical detection system as defined in claim 1 and an agri-food or pharmaceutical sample or an effluent, detecting said pathogen or said toxin by electrochemical measurement of the redox signal from the redox molecule upon interaction of said pathogen with the single-stranded oligonucleotide probe.

* * * * *